US011806344B2

(12) United States Patent
Huang et al.

(10) Patent No.: US 11,806,344 B2
(45) Date of Patent: Nov. 7, 2023

(54) PHARMACEUTICAL COMPOSITION COMPRISING MINERALOCORTICOID RECEPTOR ANTAGONIST AND USE THEREOF

(71) Applicant: KBP BIOSCIENCES PTE. LTD., Jinan (CN)

(72) Inventors: Zhenhua Huang, Jinan (CN); Xiaocui Guo, Jinan (CN)

(73) Assignee: KBP Biosciences Pte. Ltd., Singapore (SG)

( * ) Notice: Subject to any disclaimer, the term of this patent is extended or adjusted under 35 U.S.C. 154(b) by 0 days.

(21) Appl. No.: 16/068,432

(22) PCT Filed: Sep. 22, 2017

(86) PCT No.: PCT/CN2017/102969
§ 371 (c)(1),
(2) Date: Jul. 6, 2018

(87) PCT Pub. No.: WO2018/054357
PCT Pub. Date: Mar. 29, 2018

(65) Prior Publication Data
US 2019/0201390 A1 Jul. 4, 2019

(30) Foreign Application Priority Data

Sep. 24, 2016 (CN) .......................... 201610849142.4

(51) Int. Cl.
| | | |
|---|---|---|
| *A61K 31/4745* | (2006.01) | |
| *A61K 47/10* | (2017.01) | |
| *A61K 9/00* | (2006.01) | |
| *A61K 47/20* | (2006.01) | |
| *A61K 47/26* | (2006.01) | |
| *A61K 47/32* | (2006.01) | |
| *A61P 13/12* | (2006.01) | |
| *A61K 47/18* | (2017.01) | |
| *A61K 47/00* | (2006.01) | |
| *A61K 45/06* | (2006.01) | |

(52) U.S. Cl.
CPC ............ *A61K 31/4745* (2013.01); *A61K 9/00* (2013.01); *A61K 9/0053* (2013.01); *A61K 47/00* (2013.01); *A61K 47/10* (2013.01); *A61K 47/186* (2013.01); *A61K 47/20* (2013.01); *A61K 47/26* (2013.01); *A61K 47/32* (2013.01); *A61P 13/12* (2018.01); *A61K 45/06* (2013.01)

(58) Field of Classification Search
CPC .... A61K 31/4745; A61K 45/06; A61K 47/00; A61K 47/10; A61K 47/186; A61K 47/20; A61K 47/26; A61K 47/32; A61K 9/00; A61K 9/0053; A61K 2300/00; A61P 13/12
USPC ......................................................... 514/312
See application file for complete search history.

(56) References Cited

U.S. PATENT DOCUMENTS

| | | | | | |
|---|---|---|---|---|---|
| 8,946,279 | B2 * | 2/2015 | Huang | ................. | A61K 31/381 |
| | | | | | 514/406 |
| 9,468,615 | B2 * | 10/2016 | Hasse | .................. | A61K 31/275 |
| 9,468,635 | B2 * | 10/2016 | Huang | ................. | A61K 31/381 |
| 9,809,589 | B2 * | 11/2017 | Jiang | ..................... | C07D 471/04 |
| 2009/0163472 | A1 * | 6/2009 | Gavardinas | ............... | A61P 5/40 |
| | | | | | 546/199 |
| 2013/0289029 | A1 * | 10/2013 | Huang | ................... | A61K 45/06 |
| | | | | | 514/228.5 |
| 2015/0336950 | A1 * | 11/2015 | Jiang | ........................ | A61P 9/06 |
| | | | | | 546/82 |

FOREIGN PATENT DOCUMENTS

| | | |
|---|---|---|
| AU | 2017329549 | 3/2018 |
| EP | 2607363 | 6/2013 |
| EP | 2937348 | 10/2015 |
| RU | 2489432 | 8/2013 |
| WO | WO 2012022121 | 2/2012 |
| WO | WO2012022121 A1 | 2/2012 |
| WO | WO2014094664 A1 | 2/2014 |
| WO | WO 2014094664 | 6/2014 |
| WO | WO-2014094664 A1 * | 6/2014 ......... A61K 31/4745 |

OTHER PUBLICATIONS

Horiba Instruments Inc. 2012 (34 Bullsen Drive, Irvin, CA 92018, USA).*
The Rat Genome Database (RGD) https://rgd.mcw.edu/wg/ss2/ (Year: 2022).*
Lobenberg et al. "Modern bioavailability, bioequivalence and biopharmaceutics classification system. New scientific approaches to international regulatory standards," European Journal of Pharmaceutics and Biopharmaceutics 50 (2000) 3-12. (Year: 2000).*
Clinical Trial NCT02228733 published Aug. 29, 2014 (Year: 2014).*
Huang et al. (2014) "The application of allometric scaling principles to predict pharmacokinetic parameters across species," Expert Opinion on Drug Metabolism & Toxicology, 10:9, 1241-1253. (Year: 2014).*
Office Action in Australian Appln. No. 2017329549, dated Nov. 22, 2019, 4 pages.
Bakris et al., "Effect of Finerenone on Albuminuria in Patients With Diabetic Nephropathy A Randomized Clinical Trial," JAMA., 2015, 314(9):884-894.
Office Action in Cuban Appln. No. 2019-0023, dated Apr. 10, 2019, 2 pages (English translation).
Horiba Scientific A Guidebook to Particle Size Analysis, 2012.

(Continued)

*Primary Examiner* — Jeffrey S Lundgren
*Assistant Examiner* — Michael J Schmitt
(74) *Attorney, Agent, or Firm* — Fish & Richardson P.C.

(57) ABSTRACT

Provided are a pharmaceutical composition comprising a mineralocorticoid receptor antagonist and use thereof. When the pharmaceutical composition is orally administered to a patient having chronic kidney disease in need thereof, the effective and safe AUC ranges from 188 ng*h/mL to 3173 ng*h/mL, with bioavailability of 50% or more in mammals. When the pharmaceutical composition is orally administered at a daily dose of 0.1 to 1.0 mg to treat chronic kidney disease, the AUC is controlled at a safe and effective level.

22 Claims, 1 Drawing Sheet

(56) References Cited

OTHER PUBLICATIONS

Kolkhof et al., "Nonsteroidal antagonists of the mineralocorticoid receptor," Curr Opin Nephrol Hypertens, 2015, 24:417-424.
Label of Aldactone® (spironolactone tablets, USP), 2014.
Label of Inspra®, Pfizer, 2002.
Li et al., "Nanomilling of Drugs for Bioavailability Enhancement: A Holistic Formulation-Process Perspective," Pharmaceutics, 2016, 8(2):17.
Liu et al., "Finerenone: third-generation mineralocorticoid receptor antagonist for the treatment of heart failure and diabetic kidney disease," Expert Opin. Investig. Drugs, 2015, 24(8):1-13.
Nappi et al., "Aldosterone and aldosterone receptor antagonists in patients with chronic heart failure," Vascular Health and Risk Management, 2011, 7:353-363.
PCT International Search Report in International Appln. No. PCT/CN2017/102969, dated Dec. 25, 2017, 3 pages.
Shavit et al., "Aldosterone blockade and the mineralocorticoid receptor in the management of chronic kidney disease: current concepts and emerging treatment paradigms," Kidney International, 2012, 81:955-968.
The National Kidney Foundation, NKF KDOQI Clinical Practice Guidelines for Chronic Kidney Disease: Evaluation, Classification, and Stratification, 2002.
Walpole al., "The weight of nations: an estimation of adult human biomass," BMC Public Health, 2012, 12:439.
CL Office Action in Chilean Appln. No. 201900753, dated Feb. 14, 2020, 20 pages (with English translation).
IN Office Action in Indian Appln. No. 201947015188, dated Jan. 30, 2020, 5 pages (English translation).
PA Office Action in Panamanian Appln. No. 92577-01, dated Sep. 25, 2019, 2 pages (English translation).
RU Office Action in Russian Appln. No. 2019110341, dated Jan. 10, 2020, 7 pages, (English translation).
Colombian Office Action in Colombian Application No. NC2019/0003808, dated Jul. 17, 2020, 6 pages (English Translation).
Eurasian Office Action in Eurasian Application No. 201990668/28, dated Jul. 29, 2020, 5 pages.
European Search Report in European Application No. 17852425.2, dated Jun. 10, 2020, 11 pages.
ID Office Action in Indonesian Appln. No. P00201902654, dated Mar. 27, 2020, 3 pages (with English translation).
IL Office Action in Israeli Appln. No. 265560, dated Mar. 15, 2020, 4 pages (with English translation).
Khadka et al., "Pharmaceutical particle technologies: An approach to improve drug solubility, dissolution and bioavailability," Asian Journal of Pharmaceutical Sciences, Dec. 1, 2014, 9(6):304-316.
New Zealand Office Action in New Zealand Application No. 751901, dated Jul. 28, 2020, 4 pages.
Sica, "Hyperkalemia Risk in Chronic Kidney Disease Deterrent to the Use of Alsosterone Receptor Antagonism or Not," Hypertension, May 2009, 2 pages.
TN Office Action in Tunisian Appln. No. TN2019/0063, dated Aug. 22, 2019, 2 page (English Translation).
TW Office Action in Taiwan Appln. No. 106132846, dated Aug. 24, 2018, 15 pages (English Translation).
TW Office Action in Taiwan Appln. No. 106132846, dated Jan. 18, 2018, 15 pages (English Translation).
CL Office Action in Chilean Appln. No. 201900753, dated Feb. 1, 2023, 4 pages (with machine translation).
HN Office Action in Honduras Appln. No. 2019000793, dated Jan. 6, 2023, 8 pages (with English translation).
MY Office Action in Malaysia Appln. No. PI2019001497, dated Dec. 29, 2022, 3 pages.
PH Office Action in Philippines Appln. No. 1/2019/500516, dated Dec. 12, 2022, 6 pages.
EP Office Action in European Appln. No. 17852425.2, dated Mar. 3, 2023, 4 pages.
CR Office Action in Costa Rica Appln. No. 2019-0203, dated Mar. 31, 2022, 10 pages (with machine translation).
JP Office Action in Japanese Appln. No. 2019-516210, dated Feb. 1, 2022, 4 pages (with English translation).
MX Office Action in Mexican Appln. No. MX/a/2019/003339, dated Dec. 3, 2021, 8 pages (with English translation).
PH Office Action in Philippines Appln. No. 1/2019/500516, dated Jul. 15, 2022, 4 pages.
SA Office Action in Saudi Arabia Appln. No. 519401354, dated Dec. 28, 2021, 9 pages (with English translation).
SA Office Action in Saudi Arabia Appln. No. 519401354, dated Jun. 6, 2022, 9 pages (with English translation).
TW Office Action in Taiwan Appln. No. 109132042, dated Jan. 10, 2022, 10 pages (with English Translation).
TW Office Action in Taiwan Appln. No. 109132042, dated May 20, 2022, 7 pages (with English translation).
VN Office Action in Vietnam Appln. No. 1-2019-01277, dated Apr. 14, 2022, 3 pages (with English translation).
[No Author Listed], "Factors Affecting Bioavailability," New Pharmacology, Tsuji (ed.), Apr. 15, 2002, 322-334, 26 pages (with English translation).
BR Office Action in Brazilian Appln. No. 112019005214-3, dated Jun. 28, 2021, 5 pages (with English translation).
CA Office Action in Canadian Appln. No. 3037588, dated Jun. 14, 2021, 3 pages.
CL Office Action in Chilean Appln. No. 201900753, dated Feb. 21, 2020, 30 pages (with machine translation).
CN Office Action in Chinese Appln. No. 201780006183.X, dated Apr. 13, 2020, 17 pages (with English translation).
CN Office Action in Chinese Appln. No. 201780006183.X, dated Jan. 27, 2021, 17 pages (with English translation).
CO Office Action in Colombian Appln. No. NC2019/0003808, dated May 14, 2021, 15 pages (with machine translation).
CR Office Action in Costa Rica Appln. No. 2019-0203, dated Aug. 12, 2021, 8 pages (with machine translation).
CU Office Action in Cuban Appln. No. 2019-0023, dated Apr. 7, 2021, 6 pages (with English translation).
CU Office Action in Cuban Appln. No. 2019-0023, dated Jan. 25, 2021, 4 pages (English translation).
DO Office Action in Dominican Republic Appln. No. P2019-0072, dated Apr. 26, 2021, 19 pages (with machine translation).
EA Office Action in Eurasian Application No. 201990668/28, dated Mar. 2, 2021, 3 pages (with English translation).
Gupta et al., "Formulation Strategies to Improve the Bioavailability of Poorly Absorbed Drugs with Special Emphasis on Self-Emulsifying Systems," ISRN Pharm., Dec. 2013, 17 pages.
IL Office Action in Israeli Appln. No. 265560, dated Jun. 30, 2021, 11 pages (with English translation).
JP Office Action in Japanese Appln. No. 2019-516210, dated Aug. 3, 2021, 8 pages (with English translation).
KR Grant of Patent in Korean Appln. No. 20197009917, dated Feb. 23, 2021, 3 pages (with English translation).
MX Office Action in Mexican Appln. No. MX/a/2019/003339, dated Jan. 28, 2021, 4 pages (English translation).
MX Office Action in Mexican Appln. No. MX/a/2019/003339, dated Jul. 29, 2021, 10 pages (with English translation).
Nair et al., "A Simple Practice Guide for Dose Conversion Between Animals and Human," J Basic Clin Pharm, May 2016, 7(2):27-31.
NZ Office Action in New Zealand Appln. No. 751901, dated Apr. 13, 2021, 4 pages.
NZ Office Action in New Zealand Appln. No. 751901, dated Feb. 3, 2021, 4 pages.
NZ Office Action in New Zealand Appln. No. 751901, dated Jun. 2, 2021, 5 pages.
Qiu et al., "Developing Solid Oral Dosage Forms: Pharmaceutical Theory and Practice," Elsevier, 2009, 414-415, 424.
[No Author Listed], "Notice on the General Guidelines for the Clinical Evaluation of New Drugs" Yaku-Shinyaku, Jun. 1992, 43:33 pages (with English translation).
CA Office Action in Canadian Appln. No. 3037588, dated Dec. 8, 2020, 4 pages.
clinicaltrials.gov [online], "Study NCT01488877: A Study To Evaluate The Safety And Tolerability Of PF-03882845 In Patients With Type 2 Diabetic Nephropathy," Sep. 24, 2013, Version.11, retrieved from URL <https://clinicaltrials.gov/ct2/history/NCT01488877?V_11=View#StudyPageTop>, 15 pages.
CU Office Action in Cuban Appln. No. 2019-0023, dated Jul. 15, 2020, 6 pages (with English translation).

(56) References Cited

OTHER PUBLICATIONS

DO Office Action in Dominican Republic Appln. No. P2019-0072, dated Oct. 1, 2020, 6 pages (with English translation).
JP Office Action in Japanese Appln. No. 2019-516210, dated Sep. 29, 2020, 10 pages (with English translation).
KR Office Action in Korean Appln. No. 10-2019-7009917, dated Oct. 27, 2020, 9 pages (with English translation).
MA Office Action in Moroccan Appln. No. 45202, dated Nov. 13, 2020, 5 pages (with English translation).
MX Office Action in Mexican Appln. No. MX/a/2018/013985, dated Aug. 13, 2020, 9 pages (with English translation).
Orena et al., "PF-03882845, a non-steroidal mineralocorticoid receptor antagonist, prevents renal injury with reduced risk of hyperkalemia in an animal model of nephropathy," Frontiers in Pharmacology, Oct. 2013, 4(115):1-11.
RU Office Action in Russian Appln. No. 2020120876, dated Dec. 28, 2020, 13 pages (with English translation).
TH Office Action in Thailand Appln. No. 1901001650 PCT, dated Dec. 8, 2020, 8 pages (with English translation).
UA Office Action in Ukraine Appln. No. a201904176, dated Oct. 23, 2020, 10 pages (with English translation).
CO Office Action in Colombian Appln. No. NC2019/0003808, dated Oct. 14, 2021, 11 pages (with English translation).
Olyaei et al., "A Quantitative Approach to Drug Dosing in Chronic Kidney Disease," Blood Purif, Jan. 2011, 31:138-145.
Office Action in Honduras Appln. No. 2019000793, dated Jun. 22, 2023, 4 pages (with English summary).
Office Action in Peru Appln. No. 000668-2019/DIN, dated Jun. 7, 2023, 8 pages (with English summary).
CR Office Action in Costa Rica Appln. No. 2019-0203, dated Sep. 5, 2023, 16 pages (with machine translation).

\* cited by examiner

PHARMACEUTICAL COMPOSITION COMPRISING MINERALOCORTICOID RECEPTOR ANTAGONIST AND USE THEREOF

TECHNICAL FIELD

The present invention relates to the field of pharmaceutical technology and specifically describes a pharmaceutical composition comprising a mineralocorticoid receptor antagonist, use of the composition in preparation of a medicament for treating and/or preventing chronic kidney disease, and a method for treating a patient having chronic kidney disease using the composition.

BACKGROUND

Chronic kidney disease (CKD) is a type of disease with (1) 3 months or longer of kidney injury, with or without a decreased glomerular filtration rate (GFR); or (2) a glomerular filtration rate less than 60 mL/min/1.73 m² for 3 months or longer, with or without kidney injury; wherein kidney injury is defined as pathological abnormalities or markers of damage, including abnormalities in blood or urine tests or imaging studies [The National Kidney Foundation, NKF KDOQI Clinical Practice Guidelines for Chronic Kidney Disease: Evaluation, Classification, and Stratification]. Most common clinical symptoms include proteinuria (foamy urine), hematuria, edema, hypertension, increased nighttime urine, anemia, and the like. Chronic kidney disease at late stages results in chronic kidney failure, and certain clinical syndrome that develops as a systemic disorder manifested by metabolite accumulation, water/electrolyte imbalance, acidemia and etc.

Aldosterone is a steroid hormone with mineralocorticoid activity that is produced primarily by the adrenal glomerulosa [Kidney International (2012) 81, 955-968]. Aldosterone mainly functions to regulate Na+ reabsorption and K+ excretion in the distal nephron, maintaining electrolyte balance and volume homeostasis. In addition to sodium retention, aldosterone may also cause pathological progression, leading to inflammation, remodeling and fibrosis. Aldosterone activates the mineralocorticoid receptor (MR), acting on blood vessels to cause vasoconstriction. Aldosterone is also indicated to elicit renal tissue damages, resulting in increased proteinuria/albuminuria. Excessive levels of aldosterone lead to hypertension, heart failure (HF) and chronic kidney disease (CKD) [Expert Opin. Investig. Drugs (2015) 24(8), 1-13].

A mineralocorticoid receptor antagonist (MRA) binds to the mineralocorticoid receptor to block aldosterone-mineralocorticoid receptor interaction [Instruction of INSPRA, Pfizer, 2002]. The MRA has been approved to be clinically effective on patients having heart failure with reduced ejection fraction, arterial hypertension and/or chronic kidney disease [Curr Opin Nephrol Hypertens 2015, 24:417-424].

Up to now, only two steroid mineralocorticoid receptor antagonists have been developed for clinic use. Spironolactone, the first generation MRA with relatively high activity, has side effects such as gynecomastia, impotence and menstrual disturbance due to its similar structure with progesterone. Eplerenone, the second generation MRA, has improved selectivity but reduced activity [Expert Opin. Investig. Drugs (2015) 24(8), 1-13]. Both Spironolactone and Eplerenone can reduce probability of hospital admission and/or mortality rate in heart failure patients with low ejection faction; decreases the urine albumin level or urine albumin-to-creatinine ratio (UACR) and slows the progression in patients having chronic kidney disease. However, the risk of hyperkalemia development has limited the use of these two MRAs, especially in patients with kidney injuries [Expert Opin. Investig. Drugs (2015) 24(8), 1-13; Kedney International 2012; 81: 955-968]. The use of Spironolactone in patients with severe kidney damage is prohibited [Lable of Aldactone® (spironolactone tablets, USP)], while Eplerenone is contraindicated in moderate-severe kidney lesioned patients with hypertension and also those with severe kidney damages [Lable of INSPRA® (eplerenone) tablets, for oral use (USP)].

Finerenone is a non-steroid MRA being developed by Bayer and has better selectivity to MR compared to Spironolactone and higher affinity to MR compared to Eplerenone [Expert Opin. Investig. Drugs (2015) 24(8), 1-13]. Finerenone has been investigated in clinical trials for the treatment of diabetic nephrophthy (ARTS-DN), with UACR reduced by 21%, 24%, 33% and 38% in the Finerenone dosage groups at the doses of 7.5, 10, 15 and 20 mg/day, respectively. However, the onset of hyperkalemia leads to discontinuation in these groups with the incidence of 2.1%, 0%, 3.2% and 1.7%, respectively [JAMA. 2015; 314(9):884-894]. Hyperkalemia problem is evident in dosage groups where therapeutic effect is unsatisfactory.

Compound I, 2-chloro-4-[(3S,3aR)-3-cyclopentyl-7-(4-hydroxylpiperidine-1-carbonyl)-3,3a,4,5-tetrahydro-2H-pyrazolo[3,4,f]quinolin-2-yl]benzonitrile, having the following formula was disclosed in WO2012022121A1 and WO2014094664A1. This compound is also a non-steroid mineralocorticoid receptor antagonist (MRA) which shows relatively high selectivity and affinity to MRs and thus helpful in treatment of chronic kidney disease. However, as drugs targeting MRs always induce hyperkalemia, no prior art has disclosed any product containing Compound I or any method using Compound I that is proved to be safe and effective.

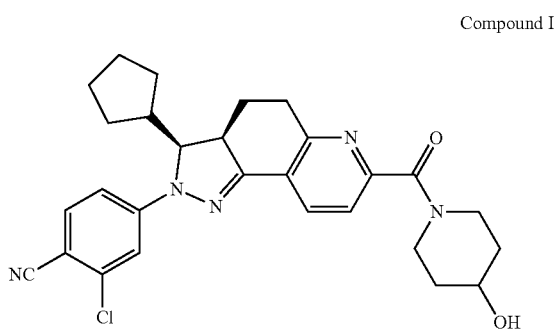 [SMILES: N#Cc1ccc(N2N=C3c4ccc(C(=O)N5CCC(O)CC5)nc4CC[C@@H]3[C@@H]2C2CCCC2)cc1Cl]

Compound I

In healthy subjects, about 90% of potassium is excreted from the kidney while the rest is excreted along with sweat and excrement. Patients having chronic kidney disease, with worsened modulatory capacity on potassium ions, is likely to develop hyperkalemia, particularly those with moderate-to-severe kidney disease.

An elevated serum potassium level brings patients with damages, especially damages to hearts. When the condition is severe, abnormal heart rhythm may occur that may result in cardiac arrest and even death. In another aspect, a high serum potassium level may also make the neuro-muscular system less excited, leading to flaccid paralysis, or induce impairment of digestive system, resulting in abdominal pain, nausea, emesia or the like.

Hyperkalemia brings injuries to patients with chronic kidney disease. It affects the depolarization and repolarization of cardiomyocytes and thus causes sluggish conduction of electrical waves and cardiac arrhythmia. With no treatment, severe hyperkalemia may cause ventricular fibrillation and cardiac arrest, resulting at sudden cardiac death.

At the current stage, there is no clinically safe and effective drug for treatment of chronic kidney disease, despite continuous demand for this. Although the mineralocorticoid receptor antagonist (MRA) has shown effects on renal disease treatment, its clinical use is constrained because of the high serum potassium level caused by its underlying action mechanism.

Therefore, it is the technical challenge to find a safe and effective drug or method for treatment of chronic kidney disease while avoiding elevated serum potassium levels.

SUMMARY OF THE INVENTION

The present inventors have found that Compound I cannot be used in safe and effective treatment of chronic kidney disease because:

(1) Compound I is a mineralocorticoid receptor antagonist which is likely to induce elevated serum potassium levels due to its action on targets; and (2) Absorption of Compound I-containing pharmaceutical composition varies among patients when it is prepared by conventional technical means.

Thus, the therapeutic window of Compound I is quite narrow in treating patients having chronic kidney disease. That is, the drug manufactured with conventional technical means do not meet clinical requirements.

In view of above, the present inventors did extensive trials and finally solves the problem. Specifically, the inventors have found the correlation between the occurrence of the elevated serum potassium level and the area under the plasma concentration-time curve (AUC), and further figured out a safe window which may produce a therapeutic effect without inducing elevated serum potassium levels. More specifically, the safe and effective AUC of Compound I ranges from 188 ng*h/mL to 3173 ng*h/mL when administered in patients having chronic kidney disease.

To achieve the safe window mentioned above, the inventors have found a safe and effective dose range and a pharmaceutical composition providing such a dose range when administered to subjects. The pharmaceutical composition of the present invention has bioavailability of 50% or more in mammals. When the pharmaceutical composition of the present invention is administered to a patient with chronic kidney disease at the dose range as claimed in the present invention, the safe and effective AUC of Compound I ranges from 188 ng*h/mL to 3173 ng*h/mL.

The present invention is directed to a pharmaceutical composition containing Compound I and a pharmaceutically acceptable carrier.

When the patient having chronic kidney disease is administered orally with the pharmaceutical composition of the present invention, the effective and safe area under the plasma concentration-time curve (AUC) of Compound I ranges from 188 ng*h/mL to 3173 ng*h/mL. According to one embodiment of the present invention, the effective and safe area under the plasma concentration-time curve (AUC) of Compound I ranges from 188 ng*h/mL to 2893 ng*h/mL. According to one embodiment of the present invention, the effective and safe area under the plasma concentration-time curve (AUC) of Compound I ranges from 188 ng*h/mL to 2613 ng*h/mL. According to one embodiment of the present invention, the effective and safe area under the plasma concentration-time curve (AUC) of Compound I ranges from 188 ng*h/mL to 1117 ng*h/mL. According to one embodiment of the present invention, the effective and safe area under the plasma concentration-time curve (AUC) of Compound I ranges from 188 ng*h/mL to 885 ng*h/mL.

Given that the bioavailability of the pharmaceutical composition of the present invention is 50% or more in mammals, to get a safe and effective AUC in patients having chronic kidney disease, the pharmaceutical composition should be administered at a daily dose of 0.1 mg to 2.5 mg of Compound I.

In one embodiment of the present invention, the pharmaceutical composition of the present invention is administered at a daily dose of 0.1 mg to 2.5 mg of Compound I in the patient to get a safe and effective AUC mentioned above. Optionally, the daily dose of Compound I ranges from 0.1 mg to 2 mg. Optionally, the daily dose of Compound I ranges from 0.1 mg to 1.5 mg. Optionally, the daily dose of Compound I ranges from 0.1 mg to 1 mg. Optionally, the daily dose of Compound I ranges from 0.1 mg to 0.9 mg. Optionally, the daily dose of Compound I ranges from 0.1 mg to 0.8 mg. Optionally, the daily dose of Compound I ranges from 0.1 mg to 0.7 mg. Optionally, the daily dose of Compound I ranges from 0.1 mg to 0.6 mg. Optionally, the daily dose of Compound I ranges from 0.1 mg to 0.5 mg. Optionally, the daily dose of Compound I ranges from 0.15 mg to 2.5 mg. Optionally, the daily dose of Compound I ranges from 0.15 mg to 2 mg. Optionally, the daily dose of Compound I ranges from 0.15 mg to 1.5 mg. Optionally, the daily dose of Compound I ranges from 0.15 mg to 1 mg. Optionally, the daily dose of Compound I ranges from 0.15 mg to 0.9 mg. Optionally, the daily dose of Compound I ranges from 0.15 mg to 0.8 mg. Optionally, the daily dose of Compound I ranges from 0.15 mg to 0.7 mg. Optionally, the daily dose of Compound I ranges from 0.15 mg to 0.6 mg. Optionally, the daily dose of Compound I ranges from 0.15 mg to 0.5 mg. Optionally, the daily dose of Compound I ranges from 0.2 mg to 2.5 mg. Optionally, the daily dose of Compound I ranges from 0.2 mg to 2 mg. Optionally, the daily dose of Compound I ranges from 0.2 mg to 1.5 mg. Optionally, the daily dose of Compound I ranges from 0.2 mg to 1 mg. Optionally, the daily dose of Compound I ranges from 0.2 mg to 0.9 mg. Optionally, the daily dose of Compound I ranges from 0.2 mg to 0.8 mg. Optionally, the daily dose of Compound I ranges from 0.2 mg to 0.7 mg. Optionally, the daily dose of Compound I ranges from 0.2 mg to 0.6 mg. Optionally, the daily dose of Compound I ranges from 0.2 mg to 0.5 mg. Optionally, the daily dose of Compound I ranges from 0.25 mg to 2.5 mg. Optionally, the daily dose of Compound I ranges from 0.25 mg to 2 mg. Optionally, the daily dose of Compound I ranges from 0.25 mg to 1.5 mg. Optionally, the daily dose of Compound I ranges from 0.25 mg to 1 mg. Optionally, the daily dose of Compound I ranges from 0.25 mg to 0.9 mg. Optionally, the daily dose of Compound I ranges from 0.25 mg to 0.8 mg. Optionally, the daily dose of Compound I ranges from 0.25 mg to 0.7 mg. Optionally, the daily dose of Compound I ranges from 0.25 mg to 0.6 mg. Optionally, the daily dose of Compound I ranges from 0.25 mg to 0.5 mg. Optionally, the daily dose of Compound I is 0.1 mg, 0.15 mg, 0.2 mg, 0.25 mg, 0.3 mg, 0.35 mg, 0.4 mg, 0.45 mg, 0.5 mg, 0.6 mg, 0.7 mg, 0.8 mg, 0.9 mg, 1 mg, 1.5 mg, 2 mg or 2.5 mg.

Compound I is insoluble in water and has a medium permeation rate. The pharmaceutical composition of this compound manufactured by conventional technical means provide low bioavailability, and enormous individual variation is observed in subjects upon administration. In order to produce a clinically acceptable effect, i.e., to treat all patients in an effective manner, it is conventional to raise the dose. However, due to the great individual variation, some patients have a rather too high AUC after administered with Compound I, resulting in increased risk of elevated serum potassium levels. Particularly, in patients having chronic kidney disease, the capacity of modulating potassium ions worsens, and the elevated serum potassium level may bring higher health risk.

The present pharmaceutical composition meets the clinical safety and efficacy requirements by lifting bioavailability to reduce individual AUC variation.

In order to lift the bioavailability of the pharmaceutical composition to a level of 50% or more in mammals, according to one embodiment of the present invention, the particle size of Compound I is decreased in the pharmaceutical composition of the present invention. According to one embodiment of the present invention, the particle-size distribution parameter $D_{90}$ of Compound I is 25 µm or less. According to one embodiment of the present invention, the particle-size distribution parameter $D_{90}$ of Compound I is 21.7 µm or less. According to one embodiment of the present invention, the particle-size distribution parameter $D_{90}$ of Compound I is 10 µm or less. According to one embodiment of the present invention, the particle-size distribution parameter $D_{90}$ of Compound I is 5 µm or less.

Compound I in the pharmaceutical composition having different particle sizes can be prepared by means of grinding, extrusion, collision, cutting, mechanical pulverization, vibrational pulverization, fluid energy milling, ultra-sonication, high pressure grinding, chemical precipitation or the like.

In order to increase the bioavailability of the pharmaceutical composition to a level of 50% or more in mammals, a surfactant is added in the pharmaceutical composition in one embodiment.

The surfactant is one or more selected from a group consisting of benzalkonium chloride, sodium laurylsulfonate, sodium dodecyl sulfate, glycerol, cholic acid, poloxamer, polyvinyl alcohol, Polysorbate 80, PVP $K_{30}$ and Polyethylene glycol. Preferably, the surfactant is one or more selected from the group consisting of benzalkonium chloride, sodium laurylsulfonate, and sodium dodecyl sulfate. Preferably, the surfactant is benzalkonium chloride, sodium laurylsulfonate, or sodium dodecyl sulfate.

In the pharmaceutical composition of the present invention, the weight ratio of Compound I to the surfactant is 1:0.1 to 1:20, preferably 1:1 to 1:20, and more preferably 1:5 to 1:20.

The present invention provides a pharmaceutical composition containing Compound I and a pharmaceutically acceptable carrier.

In one embodiment of the present invention, the pharmaceutical composition of the present invention is administered to a patient at a daily dose of 0.1 mg to 2.5 mg of Compound I. Optionally, the daily dose of Compound I ranges from 0.1 mg to 2 mg. Optionally, the daily dose of Compound I ranges from 0.1 mg to 1.5 mg. Optionally, the daily dose of Compound I ranges from 0.1 mg to 1 mg. Optionally, the daily dose of Compound I ranges from 0.1 mg to 0.9 mg. Optionally, the daily dose of Compound I ranges from 0.1 mg to 0.8 mg. Optionally, the daily dose of Compound I ranges from 0.1 mg to 0.7 mg. Optionally, the daily dose of Compound I ranges from 0.1 mg to 0.6 mg. Optionally, the daily dose of Compound I ranges from 0.1 mg to 0.5 mg. Optionally, the daily dose of Compound I ranges from 0.15 mg to 2.5 mg. Optionally, the daily dose of Compound I ranges from 0.15 mg to 2 mg. Optionally, the daily dose of Compound I ranges from 0.15 mg to 1.5 mg. Optionally, the daily dose of Compound I ranges from 0.15 mg to 1 mg. Optionally, the daily dose of Compound I ranges from 0.15 mg to 0.9 mg. Optionally, the daily dose of Compound I ranges from 0.15 mg to 0.8 mg. Optionally, the daily dose of Compound I ranges from 0.15 mg to 0.7 mg. Optionally, the daily dose of Compound I ranges from 0.15 mg to 0.6 mg. Optionally, the daily dose of Compound I ranges from 0.15 mg to 0.5 mg. Optionally, the daily dose of Compound I ranges from 0.2 mg to 2.5 mg. Optionally, the daily dose of Compound I ranges from 0.2 mg to 2 mg. Optionally, the daily dose of Compound I ranges from 0.2 mg to 1.5 mg. Optionally, the daily dose of Compound I ranges from 0.2 mg to 1 mg. Optionally, the daily dose of Compound I ranges from 0.2 mg to 0.9 mg. Optionally, the daily dose of Compound I ranges from 0.2 mg to 0.8 mg. Optionally, the daily dose of Compound I ranges from 0.2 mg to 0.7 mg. Optionally, the daily dose of Compound I ranges from 0.2 mg to 0.6 mg. Optionally, the daily dose of Compound I ranges from 0.2 mg to 0.5 mg. Optionally, the daily dose of Compound I ranges from 0.25 mg to 2.5 mg. Optionally, the daily dose of Compound I ranges from 0.25 mg to 2 mg. Optionally, the daily dose of Compound I ranges from 0.25 mg to 1.5 mg. Optionally, the daily dose of Compound I ranges from 0.25 mg to 1 mg. Optionally, the daily dose of Compound I ranges from 0.25 mg to 0.9 mg. Optionally, the daily dose of Compound I ranges from 0.25 mg to 0.8 mg. Optionally, the daily dose of Compound I ranges from 0.25 mg to 0.7 mg. Optionally, the daily dose of Compound I ranges from 0.25 mg to 0.6 mg. Optionally, the daily dose of Compound I ranges from 0.25 mg to 0.5 mg. Optionally, the daily dose of Compound I ranges from 0.3 mg to 2.5 mg. Optionally, the daily dose of Compound I ranges from 0.3 mg to 2 mg. Optionally, the daily dose of Compound I ranges from 0.3 mg to 1.5 mg. Optionally, the daily dose of Compound I ranges from 0.3 mg to 1 mg. Optionally, the daily dose of Compound I ranges from 0.3 mg to 0.9 mg. Optionally, the daily dose of Compound I ranges from 0.3 mg to 0.8 mg. Optionally, the daily dose of Compound I ranges from 0.3 mg to 0.7 mg. Optionally, the daily dose of Compound I ranges from 0.3 mg to 0.6 mg. Optionally, the daily dose of Compound I ranges from 0.3 mg to 0.5 mg. Optionally, the daily dose of Compound I is 0.1 mg, 0.15 mg, 0.2 mg, 0.25 mg, 0.3 mg, 0.35 mg, 0.4 mg, 0.45 mg, 0.5 mg, 0.6 mg, 0.7 mg, 0.8 mg, 0.9 mg, 1 mg, 1.5 mg, 2 mg or 2.5 mg.

When the patient is administered with the pharmaceutical composition of the present invention at the dose as mentioned above, the effective and safe area under the plasma concentration-time curve (AUC) of Compound I ranges from 188 ng*h/mL to 3173 ng*h/mL. According to one embodiment of the present invention, the effective and safe area under the plasma concentration-time curve (AUC) of Compound I ranges from 188 ng*h/mL to 2893 ng*h/mL. According to one embodiment of the present invention, the effective and safe area under the plasma concentration-time curve (AUC) of Compound I ranges from 188 ng*h/mL to 2613 ng*h/mL. According to one embodiment of the present invention, the effective and safe area under the plasma concentration-time curve (AUC) of Compound I ranges from 188 ng*h/mL to 1117 ng*h/mL. According to one embodiment of the present invention, the effective and safe area under the plasma concentration-time curve (AUC) of Compound I ranges from 188 ng*h/mL to 885 ng*h/mL.

Compound I is insoluble in water and has a medium permeation rate. The pharmaceutical composition of this compound manufactured by conventional technical means provide low bioavailability, and enormous individual variation is observed in subjects upon administration. In order to produce a clinically acceptable effect, i.e., to treat all patients in an effective manner, it is conventional to raise the dose. However, due to the significant individual variation, some patients have a rather too high AUC of Compound I, resulting in increased risk of elevated serum potassium levels. Particularly, in patients having chronic kidney disease, the capacity of modulating potassium ions worsens, and the elevated serum potassium level brings a higher health risk.

The present pharmaceutical composition meets the clinical safety and efficacy requirements by improving bioavailability to effectively reduce individual AUC variation.

In order to lift the bioavailability of the pharmaceutical composition to a level of 50% or more in mammals, according to one embodiment of the present invention, the particle size of Compound I is decreased in the pharmaceutical composition of the present invention. According to one embodiment of the present invention, the particle-size distribution parameter $D_{90}$ of Compound I is 25 μm or less. According to one embodiment of the present invention, the particle-size distribution parameter $D_{90}$ of Compound I is 21.7 μm or less. According to one embodiment of the present invention, the particle-size distribution parameter $D_{90}$ of Compound I is 10 μm or less. According to one embodiment of the present invention, the particle-size distribution parameter $D_{90}$ of Compound I is 5 μm or less.

Compound I in the pharmaceutical composition having different particle sizes can be prepared by means of grinding, extrusion, collision, cutting, mechanical pulverization, vibrational pulverization, fluid energy milling, ultra-sonication, high pressure grinding, chemical precipitation or the like.

In order to increase the bioavailability of the pharmaceutical composition to a level of 50% or more in mammals, according to one embodiment of the present invention, a surfactant is added in the pharmaceutical composition.

The surfactant is one or more selected from a group consisting of benzalkonium chloride, sodium lauryl sulfonate, sodium dodecyl sulfate, glycerol, cholic acid, poloxamer, polyvinyl alcohol, Polysorbate 80, PVP $K_{30}$ and Polyethylene glycol. Preferably, the surfactant is one or more selected from the group consisting of benzalkonium chloride, sodium lauryl sulfonate, and sodium dodecyl sulfate. Preferably, the surfactant is benzalkonium chloride, sodium lauryl sulfonate, or sodium dodecyl sulfate.

In the pharmaceutical composition of the present invention, the weight ratio of Compound I to the surfactant is 1:0.1 to 1:20, preferably 1:1 to 1:20, and more preferably 1:5 to 1:20.

The present invention provides a pharmaceutical composition containing Compound I and a pharmaceutically acceptable carrier.

When the patient is administered with the pharmaceutical composition of the present invention at a daily dose of 0.1 mg to 2.5 mg of Compound I, the safe and effective area under the plasma concentration-time curve (AUC) ranges from 188 ng*h/mL to 3173 ng*h/mL.

With respect to the pharmaceutical composition of the present invention, optionally, the daily dose of Compound I ranges from 0.1 mg to 2.5 mg. Optionally, the daily dose of Compound I ranges from 0.1 mg to 2 mg. Optionally, the daily dose of Compound I ranges from 0.1 mg to 1.5 mg. Optionally, the daily dose of Compound I ranges from 0.1 mg to 1 mg. Optionally, the daily dose of Compound I ranges from 0.1 mg to 0.9 mg. Optionally, the daily dose of Compound I ranges from 0.1 mg to 0.8 mg. Optionally, the daily dose of Compound I ranges from 0.1 mg to 0.7 mg. Optionally, the daily dose of Compound I ranges from 0.1 mg to 0.6 mg. Optionally, the daily dose of Compound I ranges from 0.1 mg to 0.5 mg. Optionally, the daily dose of Compound I ranges from 0.15 mg to 2.5 mg. Optionally, the daily dose of Compound I ranges from 0.15 mg to 2 mg. Optionally, the daily dose of Compound I ranges from 0.15 mg to 1.5 mg. Optionally, the daily dose of Compound I ranges from 0.15 mg to 1 mg. Optionally, the daily dose of Compound I ranges from 0.15 mg to 0.9 mg. Optionally, the daily dose of Compound I ranges from 0.15 mg to 0.8 mg. Optionally, the daily dose of Compound I ranges from 0.15 mg to 0.7 mg. Optionally, the daily dose of Compound I ranges from 0.15 mg to 0.6 mg. Optionally, the daily dose of Compound I ranges from 0.15 mg to 0.5 mg. Optionally, the daily dose of Compound I ranges from 0.2 mg to 2.5 mg. Optionally, the daily dose of Compound I ranges from 0.2 mg to 2 mg. Optionally, the daily dose of Compound I ranges from 0.2 mg to 1.5 mg. Optionally, the daily dose of Compound I ranges from 0.2 mg to 1 mg. Optionally, the daily dose of Compound I ranges from 0.2 mg to 0.9 mg. Optionally, the daily dose of Compound I ranges from 0.2 mg to 0.8 mg. Optionally, the daily dose of Compound I ranges from 0.2 mg to 0.7 mg. Optionally, the daily dose of Compound I ranges from 0.2 mg to 0.6 mg. Optionally, the daily dose of Compound I ranges from 0.2 mg to 0.5 mg. Optionally, the daily dose of Compound I ranges from 0.25 mg to 2.5 mg. Optionally, the daily dose of Compound I ranges from 0.25 mg to 2 mg. Optionally, the daily dose of Compound I ranges from 0.25 mg to 1.5 mg. Optionally, the daily dose of Compound I ranges from 0.25 mg to 1 mg. Optionally, the daily dose of Compound I ranges from 0.25 mg to 0.9 mg. Optionally, the daily dose of Compound I ranges from 0.25 mg to 0.8 mg. Optionally, the daily dose of Compound I ranges from 0.25 mg to 0.7 mg. Optionally, the daily dose of Compound I ranges from 0.25 mg to 0.6 mg. Optionally, the daily dose of Compound I ranges from 0.25 mg to 0.5 mg. Optionally, the daily dose of Compound I ranges from 0.3 mg to 2.5 mg. Optionally, the daily dose of Compound I ranges from 0.3 mg to 2 mg. Optionally, the daily dose of Compound I ranges from 0.3 mg to 1.5 mg. Optionally, the daily dose of Compound I ranges from 0.3 mg to 1 mg. Optionally, the daily dose of Compound I ranges from 0.3 mg to 0.9 mg. Optionally, the daily dose of Compound I ranges from 0.3 mg to 0.8 mg. Optionally, the daily dose of Compound I ranges from 0.3 mg to 0.7 mg. Optionally, the daily dose of Compound I ranges from 0.3 mg to 0.6 mg. Optionally, the daily dose of Compound I ranges from 0.3 mg to 0.5 mg. Optionally, the daily dose of Compound I is 0.1 mg, 0.15 mg, 0.2 mg, 0.25 mg, 0.3 mg, 0.35 mg, 0.4 mg, 0.45 mg, 0.5 mg, 0.6 mg, 0.7 mg, 0.8 mg, 0.9 mg, 1 mg, 1.5 mg, 2 mg or 2.5 mg.

According to one embodiment, when the patient is administered with the pharmaceutical composition of the present invention, the effective and safe area under the plasma concentration-time curve (AUC) of Compound I ranges from 188 ng*h/mL to 2893 ng*h/mL. According to one embodiment of the present invention, the effective and safe area under the plasma concentration-time curve (AUC) of Compound I ranges from 188 ng*h/mL to 2613 ng*h/mL. According to one embodiment of the present invention, the effective and safe area under the plasma concentration-time curve (AUC) of Compound I ranges from 188 ng*h/mL to 1117 ng*h/mL. According to one embodiment of the present invention, the effective and safe area under the plasma concentration-time curve (AUC) of Compound I ranges from 188 ng*h/mL to 885 ng*h/mL.

Compound I is insoluble in water and has a medium permeation rate. The pharmaceutical composition of this compound manufactured by conventional technical means provide low bioavailability, and enormous individual variation is observed in subjects upon administration. In order to produce a clinically acceptable effect, i.e., to treat all patients in an effective manner, it is conventional to raise the dose. However, due to the significant individual variation, some patients have a rather too high AUC of Compound I, resulting in increased risk of elevated serum potassium levels. Particularly, in patients having chronic kidney disease, the capacity of modulating potassium ions worsens, and the elevated serum potassium level brings a higher health risk.

The present pharmaceutical composition meets the clinical safety and efficacy requirements by improving bioavailability to effectively reduce individual AUC variation.

In order to lift the bioavailability of the pharmaceutical composition to a level of 50% or more in mammals, according to one embodiment of the present invention, the particle size of Compound I is decreased in the pharmaceutical composition of the present invention. According to one embodiment of the present invention, the particle-size distribution parameter $D_{90}$ of Compound I is 25 µm or less. According to one embodiment of the present invention, the particle-size distribution parameter $D_{90}$ of Compound I is 21.7 µm or less. According to one embodiment of the present invention, the particle-size distribution parameter $D_{90}$ of Compound I is 10 µm or less. According to one embodiment of the present invention, the particle-size distribution parameter $D_{90}$ of Compound I is 5 µm or less.

Compound I in the pharmaceutical composition having different particle sizes can be prepared by means of grinding, extrusion, collision, cutting, mechanical pulverization, vibrational pulverization, fluid energy milling, ultra-sonication, high pressure grinding, chemical precipitation or the like.

In order to increase the bioavailability of the pharmaceutical composition to a level of 50% or more in mammals, according to one embodiment of the present invention, a surfactant is added in the pharmaceutical composition.

The surfactant is one or more selected from a group consisting of benzalkonium chloride, sodium lauryl sulfonate, sodium dodecyl sulfate, glycerol, cholic acid, poloxamer, polyvinyl alcohol, Polysorbate 80, PVP $K_{30}$ and Polyethylene glycol. Preferably, the surfactant is one or more selected from the group consisting of benzalkonium chloride, sodium lauryl sulfonate, and sodium dodecyl sulfate. Preferably, the surfactant is benzalkonium chloride, sodium lauryl sulfonate, or sodium dodecyl sulfate.

In the pharmaceutical composition of the present invention, the weight ratio of Compound I to the surfactant is 1:0.1 to 1:20, preferably 1:1 to 1:20, and more preferably 1:5 to 1:20.

The present invention provides the use of the pharmaceutical composition in preparation of a medicament for treating and/or preventing chronic kidney disease.

When a subject in need thereof is administered orally with the pharmaceutical composition of the present invention, the effective and safe area under the plasma concentration-time curve (AUC) of Compound I ranges from 188 ng*h/mL to 3173 ng*h/mL. According to one embodiment of the present invention, the effective and safe area under the plasma concentration-time curve (AUC) of Compound I ranges from 188 ng*h/mL to 2893 ng*h/mL. According to one embodiment of the present invention, the effective and safe area under the plasma concentration-time curve (AUC) of Compound I ranges from 188 ng*h/mL to 2613 ng*h/mL. According to one embodiment of the present invention, the effective and safe area under the plasma concentration-time curve (AUC) of Compound I ranges from 188 ng*h/mL to 1117 ng*h/mL. According to one embodiment of the present invention, the effective and safe area under the plasma concentration-time curve (AUC) of Compound I ranges from 188 ng*h/mL to 885 ng*h/mL.

In one embodiment of the present invention, in order to provide the subject/patient with a safe and effective AUC range mentioned above, the subject/patient is administered with the pharmaceutical composition at a daily dose of 0.1 mg to 2.5 mg of Compound I. Optionally, the daily dose of Compound I ranges from 0.1 mg to 2 mg. Optionally, the daily dose of Compound I ranges from 0.1 mg to 1.5 mg. Optionally, the daily dose of Compound I ranges from 0.1 mg to 1 mg. Optionally, the daily dose of Compound I ranges from 0.1 mg to 0.9 mg. Optionally, the daily dose of Compound I ranges from 0.1 mg to 0.8 mg. Optionally, the daily dose of Compound I ranges from 0.1 mg to 0.7 mg. Optionally, the daily dose of Compound I ranges from 0.1 mg to 0.6 mg. Optionally, the daily dose of Compound I ranges from 0.1 mg to 0.5 mg. Optionally, the daily dose of Compound I ranges from 0.15 mg to 2.5 mg. Optionally, the daily dose of Compound I ranges from 0.15 mg to 2 mg. Optionally, the daily dose of Compound I ranges from 0.15 mg to 1.5 mg. Optionally, the daily dose of Compound I ranges from 0.15 mg to 1 mg. Optionally, the daily dose of Compound I ranges from 0.15 mg to 0.9 mg. Optionally, the daily dose of Compound I ranges from 0.15 mg to 0.8 mg. Optionally, the daily dose of Compound I ranges from 0.15 mg to 0.7 mg. Optionally, the daily dose of Compound I ranges from 0.15 mg to 0.6 mg. Optionally, the daily dose of Compound I ranges from 0.15 mg to 0.5 mg. Optionally, the daily dose of Compound I ranges from 0.2 mg to 2.5 mg. Optionally, the daily dose of Compound I ranges from 0.2 mg to 2 mg. Optionally, the daily dose of Compound I ranges from 0.2 mg to 1.5 mg. Optionally, the daily dose of Compound I ranges from 0.2 mg to 1 mg. Optionally, the daily dose of Compound I ranges from 0.2 mg to 0.9 mg. Optionally, the daily dose of Compound I ranges from 0.2 mg to 0.8 mg. Optionally, the daily dose of Compound I ranges from 0.2 mg to 0.7 mg. Optionally, the daily dose of Compound I ranges from 0.2 mg to 0.6 mg. Optionally, the daily dose of Compound I ranges from 0.2 mg to 0.5 mg. Optionally, the daily dose of Compound I ranges from 0.25 mg to 2.5 mg. Optionally, the daily dose of Compound I ranges from 0.25 mg to 2 mg. Optionally, the daily dose of Compound I ranges from 0.25 mg to 1.5 mg. Optionally, the daily dose of Compound I ranges from 0.25 mg to 1 mg. Optionally, the daily dose of Compound I ranges from 0.25 mg to 0.9 mg. Optionally, the daily dose of Compound I ranges from 0.25 mg to 0.8 mg. Optionally, the daily dose of Compound I ranges from 0.25 mg to 0.7 mg. Optionally, the daily dose of Compound I ranges from 0.25 mg to 0.6 mg. Optionally, the daily dose of Compound I ranges from 0.25 mg to 0.5 mg. Optionally, the daily dose of Compound I ranges from 0.3 mg to 2.5 mg. Optionally, the daily dose of Compound I ranges from 0.3 mg to 2 mg. Optionally, the daily dose of Compound I ranges from 0.3 mg to 1.5 mg. Optionally, the daily dose of Compound I ranges from 0.3 mg to 1 mg. Optionally, the daily dose of Compound I ranges from 0.3 mg to 0.9 mg. Optionally, the daily dose of Compound I ranges from 0.3 mg to 0.8 mg. Optionally, the daily dose of Compound I ranges from 0.3 mg to 0.7 mg. Optionally, the daily dose of Compound I ranges from 0.3 mg to 0.6 mg. Optionally, the daily dose of Compound I ranges from 0.3 mg to 0.5 mg. Optionally, the daily dose of Compound I is 0.1 mg, 0.15 mg, 0.2 mg, 0.25 mg, 0.3 mg, 0.35 mg, 0.4 mg, 0.45 mg, 0.5 mg, 0.6 mg, 0.7 mg, 0.8 mg, 0.9 mg, 1 mg, 1.5 mg, 2 mg or 2.5 mg.

Compound I is insoluble in water and has a medium permeation rate. The pharmaceutical composition of this compound manufactured by conventional technical means provide low bioavailability, and enormous individual variation is observed in subjects upon administration. In order to produce a clinically acceptable effect, i.e., to treat all patients in an effective manner, it is conventional to raise the dose. However, due to the significant individual variation, some patients have a rather too high AUC of Compound I, resulting in increased risk of elevated serum potassium levels. Particularly, in patients having chronic kidney disease, the capacity of modulating potassium ions worsens, and the elevated serum potassium level brings a higher health risk.

The present pharmaceutical composition meets the clinical safety and efficacy requirements by improving bioavailability to effectively reduce individual AUC variation.

In order to lift the bioavailability of the pharmaceutical composition to a level of 50% or more in mammals, according to one embodiment of the present invention, the particle size of Compound I is decreased in the pharmaceutical composition of the present invention. According to one embodiment of the present invention, the particle-size distribution parameter $D_{90}$ of Compound I is 25 μm or less. According to one embodiment of the present invention, the particle-size distribution parameter $D_{90}$ of Compound I is 21.7 μm or less. According to one embodiment of the present invention, the particle-size distribution parameter $D_{90}$ of Compound I is 10 μm or less. According to one embodiment of the present invention, the particle-size distribution parameter $D_{90}$ of Compound I is 5 μm or less.

Compound I in the pharmaceutical composition having different particle sizes can be prepared by means of grinding, extrusion, collision, cutting, mechanical pulverization, vibrational pulverization, fluid energy milling, ultra-sonication, high pressure grinding, chemical precipitation or the like.

In order to increase the bioavailability of the pharmaceutical composition to a level of 50% or more in mammals, according to one embodiment of the present invention, a surfactant is added in the pharmaceutical composition.

The surfactant is one or more selected from a group consisting of benzalkonium chloride, sodium lauryl sulfonate, sodium dodecyl sulfate, glycerol, cholic acid, poloxamer, polyvinyl alcohol, Polysorbate 80, PVP $K_{30}$ and Polyethylene glycol. Preferably, the surfactant is one or more selected from the group consisting of benzalkonium chloride, sodium lauryl sulfonate, and sodium dodecyl sulfate. Preferably, the surfactant is benzalkonium chloride, sodium lauryl sulfonate, or sodium dodecyl sulfate.

In the pharmaceutical composition of the present invention, the weight ratio of Compound I to the surfactant is 1:0.1 to 1:20, preferably 1:1 to 1:20, and more preferably 1:5 to 1:20.

The present invention provides a pharmaceutical composition comprising Compound I and a pharmaceutically acceptable carrier.

In one embodiment of the present invention, a patient is administered with the pharmaceutical composition at a daily dose of 0.1 mg to 2.5 mg of Compound I. Optionally, the daily dose of Compound I ranges from 0.1 mg to 2 mg. Optionally, the daily dose of Compound I ranges from 0.1 mg to 1.5 mg. Optionally, the daily dose of Compound I ranges from 0.1 mg to 1 mg. Optionally, the daily dose of Compound I ranges from 0.1 mg to 0.9 mg. Optionally, the daily dose of Compound I ranges from 0.1 mg to 0.8 mg. Optionally, the daily dose of Compound I ranges from 0.1 mg to 0.7 mg. Optionally, the daily dose of Compound I ranges from 0.1 mg to 0.6 mg. Optionally, the daily dose of Compound I ranges from 0.1 mg to 0.5 mg. Optionally, the daily dose of Compound I ranges from 0.15 mg to 2.5 mg. Optionally, the daily dose of Compound I ranges from 0.15 mg to 2 mg. Optionally, the daily dose of Compound I ranges from 0.15 mg to 1.5 mg. Optionally, the daily dose of Compound I ranges from 0.15 mg to 1 mg. Optionally, the daily dose of Compound I ranges from 0.15 mg to 0.9 mg. Optionally, the daily dose of Compound I ranges from 0.15 mg to 0.8 mg. Optionally, the daily dose of Compound I ranges from 0.15 mg to 0.7 mg. Optionally, the daily dose of Compound I ranges from 0.15 mg to 0.6 mg. Optionally, the daily dose of Compound I ranges from 0.15 mg to 0.5 mg. Optionally, the daily dose of Compound I ranges from 0.2 mg to 2.5 mg. Optionally, the daily dose of Compound I ranges from 0.2 mg to 2 mg. Optionally, the daily dose of Compound I ranges from 0.2 mg to 1.5 mg. Optionally, the daily dose of Compound I ranges from 0.2 mg to 1 mg. Optionally, the daily dose of Compound I ranges from 0.2 mg to 0.9 mg. Optionally, the daily dose of Compound I ranges from 0.2 mg to 0.8 mg. Optionally, the daily dose of Compound I ranges from 0.2 mg to 0.7 mg. Optionally, the daily dose of Compound I ranges from 0.2 mg to 0.6 mg. Optionally, the daily dose of Compound I ranges from 0.2 mg to 0.5 mg. Optionally, the daily dose of Compound I ranges from 0.25 mg to 2.5 mg. Optionally, the daily dose of Compound I ranges from 0.25 mg to 2 mg. Optionally, the daily dose of Compound I ranges from 0.25 mg to 1.5 mg. Optionally, the daily dose of Compound I ranges from 0.25 mg to 1 mg. Optionally, the daily dose of Compound I ranges from 0.25 mg to 0.9 mg. Optionally, the daily dose of Compound I ranges from 0.25 mg to 0.8 mg. Optionally, the daily dose of Compound I ranges from 0.25 mg to 0.7 mg. Optionally, the daily dose of Compound I ranges from 0.25 mg to 0.6 mg. Optionally, the daily dose of Compound I ranges from 0.25 mg to 0.5 mg. Optionally, the daily dose of Compound I ranges from 0.3 mg to 2.5 mg. Optionally, the daily dose of Compound I ranges from 0.3 mg to 2 mg. Optionally, the daily dose of Compound I ranges from 0.3 mg to 1.5 mg. Optionally, the daily dose of Compound I ranges from 0.3 mg to 1 mg. Optionally, the daily dose of Compound I ranges from 0.3 mg to 0.9 mg. Optionally, the daily dose of Compound I ranges from 0.3 mg to 0.8 mg. Optionally, the daily dose of Compound I ranges from 0.3 mg to 0.7 mg. Optionally, the daily dose of Compound I ranges from 0.3 mg to 0.6 mg. Optionally, the daily dose of Compound I ranges from 0.3 mg to 0.5 mg. Optionally, the daily dose of Compound I is 0.1 mg, 0.15 mg, 0.2 mg, 0.25 mg, 0.3 mg, 0.35 mg, 0.4 mg, 0.45 mg, 0.5 mg, 0.6 mg, 0.7 mg, 0.8 mg, 0.9 mg, 1 mg, 1.5 mg, 2 mg or 2.5 mg.

Compound I is insoluble in water and has a medium permeation rate. The pharmaceutical composition of this compound manufactured by conventional technical means provide low bioavailability, and enormous individual variation is observed in subjects upon administration. In order to produce a clinically acceptable effect, i.e., to treat all patients in an effective manner, it is conventional to raise the dose. However, due to the significant individual variation, some patients have a rather too high AUC of Compound I, resulting in increased risk of elevated serum potassium levels. Particularly, in patients having chronic kidney disease, the capacity of modulating potassium ions worsens, and the elevated serum potassium level brings a higher health risk.

The present pharmaceutical composition meets the clinical safety and efficacy requirements by improving bioavailability to effectively reduce individual AUC variation.

In order to lift the bioavailability of the pharmaceutical composition to a level of 50% or more in mammals, according to one embodiment of the present invention, the particle size of Compound I is decreased in the pharmaceutical composition of the present invention. According to one embodiment of the present invention, the particle-size distribution parameter $D_{90}$ of Compound I is 25 µm or less. According to one embodiment of the present invention, the particle-size distribution parameter $D_{90}$ of Compound I is 21.7 µm or less. According to one embodiment of the present invention, the particle-size distribution parameter $D_{90}$ of Compound I is 5 µm or less.

Compound I in the pharmaceutical composition having different particle sizes can be prepared by means of grinding, extrusion, collision, cutting, mechanical pulverization, vibrational pulverization, fluid energy milling, ultra-sonication, high pressure grinding, chemical precipitation or the like.

In order to increase the bioavailability of the pharmaceutical composition to a level of 50% or more in mammals, according to one embodiment of the present invention, a surfactant is added in the pharmaceutical composition.

The surfactant is one or more selected from a group consisting of benzalkonium chloride, sodium lauryl sulfonate, sodium dodecyl sulfate, glycerol, cholic acid, poloxamer, polyvinyl alcohol, Polysorbate 80, PVP $K_{30}$ and Polyethylene glycol. Preferably, the surfactant is one or more selected from the group consisting of benzalkonium chloride, sodium lauryl sulfonate, and sodium dodecyl sulfate. Preferably, the surfactant is benzalkonium chloride, sodium lauryl sulfonate, or sodium dodecyl sulfate.

In the pharmaceutical composition of the present invention, the weight ratio of Compound I to the surfactant is 1:0.1 to 1:20, preferably 1:1 to 1:20, and more preferably 1:5 to 1:20.

The pharmaceutical composition of the present invention can be prepared as an oral formulation, more preferably as tablets, extended-release tablets, capsules, granules, soft capsules, dripping pills, micro-capsules, micro-spheres, liposomes, a self-emulsifying drug delivery system, solid dispersions, micelles, oral melt tablets, solutions, suspensions, or emulsions.

A single formulation of the pharmaceutical composition of the present invention contains 0.01 mg to 2.5 mg of Compound I, optionally 0.01 mg to 2 mg of Compound I, optionally 0.01 mg to 1.5 mg of Compound I, optionally 0.01 mg to 1 mg of Compound I, optionally 0.01 mg to 0.9 mg of Compound I, optionally 0.01 mg to 0.8 mg of Compound I, optionally 0.01 mg to 0.7 mg of Compound I, optionally 0.01 mg to 0.6 mg of Compound I, optionally 0.01 mg to 0.5 mg of Compound I, optionally 0.025 mg to 2.5 mg of Compound I, optionally 0.025 mg to 2 mg of Compound I, optionally 0.025 mg to 1.5 mg of Compound I, optionally 0.025 mg to 1 mg of Compound I, optionally 0.025 mg to 0.9 mg of Compound I, optionally 0.025 mg to 0.8 mg of Compound I, optionally 0.025 mg to 0.7 mg of Compound I, optionally 0.025 mg to 0.6 mg of Compound I, optionally 0.025 mg to 0.5 mg of Compound I, optionally 0.05 mg to 2.5 mg of Compound I, optionally 0.05 mg to 2 mg of Compound I, optionally 0.05 mg to 1.5 mg of Compound I, optionally 0.05 mg to 1 mg of Compound I, optionally 0.05 mg to 0.9 mg of Compound I, optionally 0.05 mg to 0.8 mg of Compound I, optionally 0.05 mg to 0.7 mg of Compound I, optionally 0.05 mg to 0.6 mg of Compound I, optionally 0.05 mg to 0.5 mg of Compound I, optionally 0.1 mg to 2.5 mg of Compound I, optionally 0.1 mg to 2 mg of Compound I, optionally 0.1 mg to 1.5 mg of Compound I, optionally 0.1 mg to 1 mg of Compound I, optionally 0.1 mg to 0.9 mg of Compound I, optionally 0.1 mg to 0.8 mg of Compound I, optionally 0.1 mg to 0.7 mg of Compound I, optionally 0.1 mg to 0.6 mg of Compound I, optionally 0.1 mg to 0.5 mg of Compound I, optionally 0.15 mg to 2.5 mg of Compound I, optionally 0.15 mg to 2 mg of Compound I, optionally 0.15 mg to 1.5 mg of Compound I, optionally 0.15 mg to 1 mg of Compound I, optionally 0.15 mg to 0.9 mg of Compound I, optionally 0.15 mg to 0.8 mg of Compound I, optionally 0.15 mg to 0.7 mg of Compound I, optionally 0.15 mg to 0.6 mg of Compound I, optionally 0.15 mg to 0.5 mg of Compound I, optionally 0.2 mg to 2.5 mg of Compound I, optionally 0.2 mg to 2 mg of Compound I, optionally 0.2 mg to 1.5 mg of Compound I, optionally 0.2 mg to 1 mg of Compound I, optionally 0.2 mg to 0.9 mg of Compound I, optionally 0.2 mg to 0.8 mg of Compound I, optionally 0.2 mg to 0.7 mg of Compound I, optionally 0.2 mg to 0.6 mg of Compound I, optionally 0.2 mg to 0.5 mg of Compound I, optionally 0.25 mg to 2.5 mg of Compound I, optionally 0.25 mg to 2 mg of Compound I, optionally 0.25 mg to 1.5 mg of Compound I, optionally 0.25 mg to 1 mg of Compound I, optionally 0.25 mg to 0.9 mg of Compound I, optionally 0.25 mg to 0.8 mg of Compound I, optionally 0.25 mg to 0.7 mg of Compound I, optionally 0.25 mg to 0.6 mg of Compound I, optionally 0.25 mg to 0.5 mg of Compound I, optionally 0.3 mg to 2.5 mg of Compound I, optionally 0.3 mg to 2 mg of Compound I, optionally 0.3 mg to 1.5 mg of Compound I, optionally 0.3 mg to 1 mg of Compound I, optionally 0.3 mg to 0.9 mg of Compound I, optionally 0.3 mg to 0.8 mg of Compound I, optionally 0.3 mg to 0.7 mg of Compound I, optionally 0.3 mg to 0.6 mg of Compound I, optionally 0.3 mg to 0.5 mg of Compound I, optionally 0.01 mg, 0.025 mg, 0.05 mg, 0.1 mg, 0.15 mg, 0.2 mg, 0.25 mg, 0.3 mg, 0.35 mg, 0.4 mg, 0.45 mg, 0.5 mg, 0.6 mg, 0.7 mg, 0.8 mg, 0.9 mg, 1 mg, 1.5 mg, 2 mg, or 2.5 mg of Compound I.

The pharmaceutical composition of the present invention can readily block the binding of the mineralocorticoid receptor to the aldosterone. According to the underlying pharmacological action, the pharmaceutical composition can be used to specifically treat and/or prevent chronic kidney disease selected from the group consisting of hypertensive nephropathy, diabetic nephropathy, glomerulonephritis, renal failure, albuminuria, acute kidney injury, and kidney cyst; chronic kidney disease with hypertension, chronic kidney disease with heart failure, chronic kidney disease with hypertension and heart failure, chronic kidney disease with obesity, chronic kidney disease with hyperlipoidemia, chronic kidney disease with diabetes mellitus, and cardiorenal syndrome; cardiovascular diseases selected from the group consisting of hypertension, heart failure (i.e., congestive heart failure, selected from the group consisting of heart failure with low ejection fraction, heart failure with normal ejection fraction, and acute heart failure), myocardial infarction, angina pectoris, cardiac hypertrophy, myocarditis, heart vascular fibrosis, baroreceptor dysfunction, fluid overload and cardiac arrhythmia, hyperlipoidemia and obesity; endocrine diseases selected from the group consisting of primary and secondary hyperaldosteronism, Addison's disease, Cushing's syndrome, and Bartter syndrome. Particularly, the pharmaceutical composition of the present invention can be used to treat and/or prevent chronic kidney disease, including diabetic nephropathy, and hypertensive nephropathy; chronic kidney disease with hypertension and/or heart failure; heart failure, and/or hypertension.

In one embodiment, the present invention further discloses the use of the pharmaceutical composition in the preparation of a medicament for treatment of chronic kidney disease, heart failure and hypertension.

In another embodiment, the present invention is directed to a method for treating chronic kidney disease, heart failure and/or hypertension, comprising administering a subject in need thereof with a therapeutically effective amount of the pharmaceutical composition of the present invention.

The subject of the present invention may be mammals, preferably human beings, particularly those having the disease selected from the group consisting of chronic kidney disease, selected from the group consisting of hypertensive nephropathy, diabetic nephropathy, glomerulonephritis, renal failure, albuminuria, kidney cyst, and glomerulosclerosis; chronic kidney disease with hypertension, chronic kidney disease with heart failure, chronic kidney disease with hypertension and heart failure, chronic kidney disease with obesity, chronic kidney disease with hyperlipoidemia, chronic kidney disease with diabetes mellitus, and cardiorenal syndrome; cardiovascular diseases, selected from the group consisting of hypertension, heart failure (i.e., congestive heart failure, selected from the group consisting of heart failure with low ejection fraction, heart failure with normal ejection fraction, and acute heart failure), myocardial infarction, angina pectoris, cardiac hypertrophy, myocarditis, heart vascular fibrosis, myocardial ischemia, coronary heart disease, coronary artery disease, baroreceptor dysfunction, fluid overload and cardiac arrhythmia, hyperlipoidemia and obesity; endocrine diseases, selected from the group consisting of primary and secondary hyperaldosteronism, Addison's disease, Cushing's syndrome, and Bartter syndrome. Particularly, the subject is one having the disease selected from chronic kidney disease, selected from the group consisting of hypertensive nephropathy, diabetic nephropathy, glomerulonephritis, renal failure, albuminuria, kidney cyst, and glomerulosclerosis; chronic kidney disease with hypertension, chronic kidney disease with heart failure, chronic kidney disease with hypertension and heart failure, chronic kidney disease with obesity, chronic kidney disease with hyperlipoidemia, chronic kidney disease with diabetes mellitus, and cardiorenal syndrome.

In an embodiment, the pharmaceutical composition of the present invention can be administered once or for several times per day. Preferably, the pharmaceutical composition is administered once a day at the dose mentioned above. The pharmaceutical composition of the present invention can be administered at any time of the day.

The pharmaceutical composition of the present invention can be used to treat the subject in need thereof in combination with some other agents which can be one or two selected from the group consisting of an antihypertensive agent, an antilipemic agent, and an antidiabetic agent.

The antihypertensive agent can be an angiotensin converting enzyme inhibitor, an angiotensin II receptor blocker, a renin inhibitor, a calcium channel blocker, a diuretic, a beta-receptor blocker, or an alpha-receptor blocker. Specifically, antihypertensive agent includes, but not limited to, the angiotensin converting enzyme inhibitor, selected from the group consisting of Captopril, Enalapril, Benazepril, Delapril, Lisinopril, and Perindopril; the angiotensin II receptor blocker, selected from the group consisting of Losartan, Valsartan, Irbesartan, Candesartan, Telmisartan, Eprosartan, and Irbesartan; the renin inhibitor, selected from the group consisting of Aliskiren and Aliskiren; the calcium channel blocker, selected from the group consisting of Nifedipine, Amlodipine, Lercanidipine, Nimodipine, Nicardipine, Nitrendipine, Nisoldipine, Felodipine, Benidipine, Lacidipine, Diltiazem, Verapamil, Flunarizine, Cinnarizine, and Lidoflazine; the diuretic, selected from the group consisting of Chlorothiazide, Chlortralidone, and Furosemide; the beta-receptor blocker, selected from the group consisting of Atenolol, Metoprolol, Sotaol hydrochloride, Propranolol Hydrochloride, and Carvedilol; and the alpha-receptor blocker, selected from the group consisting of Phentolamine, Tolazoline, Phenoxybenzamine, and Prazosin.

The antilipemic agent is selected from the group consisting of Atorvastatin, Lovastatin, Simvastatin, Pravastatin, fluvastatin, Rosuvastatin, Ciprofibrate, Bezafibrate, Fenofibrate, and Gemfibrozil.

The antidiabetic agent is selected from the group consisting of an insulinotropic agent, metformins, an alpha-glucosidase inhibitor, a thiazolidinedione derived sensitizing agent, a Meglitinide derived insulinotropic agent, a GLP-1 receptor agonist, and a DPP-4 inhibitor. The antidiabetic agent includes, but not limited to, a sulfonylureas insulinotropic agent, selected from the group consisting of Glipizide, Gliclazide, Glibenclamide, Glibornuride, Glimepiride, and Gliquidone; a non-sulfonylureas Meglitinide derived insulinotropic agent, selected from the group consisting of Repaglinide and Nateglinide; metformins, selected from metformin; an alpha-glucosidase inhibitor, selected from the group consisting of Bose-100, Acarbose, and Voglibose; an insulin sensitizing agent, selected from Rosiglitazone, and Pioglitazone; a dipeptidyl peptidase 4 (DPP-4) inhibitor, selected from the group consisting of Sitagliptin, Saxagliptin, and Vildagliptin; and a GLP-1 receptor agonist, selected from Exenatide, and Liraglutide.

Compound I is a mineralocorticoid receptor antagonist. Its clinical use causes a risk of elevated serum potassium levels due to its underlying action mechanism. A patient having chronic kidney disease, because of worsened capacity of modulating potassium ions, is likely to develop hyperkalemia upon administration of this compound. Hyperkalemia brings great injuries to, or even poses lethal risk on a patient having chronic kidney disease. Thus, the application of the MRA drugs are largely constrained, and no MRA drug has been approved till now to treat chronic kidney disease and related complications.

In order to safely and effectively use Compound I in clinical treatment of chronic kidney disease to which no drug is clinically approved up to now, the inventors did extensive experiments on Compound I and finally found the safe and effective window. They later, based on the safe and effective window, found the safe and effective dose range of Compound I and invented a pharmaceutical composition having bioavailability of 50% or more in mammals.

I. The Pharmaceutical Composition of the Present Invention has a Narrow Safe and Effective Window With clinical trials, Compound I was found to have a very narrow safe window in patients with chronic kidney disease, i.e., it is safe and effective when AUC is in the range of 188 ng*h/mL to 3173 ng*h/mL.

i. A Wide Safe Window was Found in SD Rats

In the toxicity testing experiment and the pharmacokinetical study where male SD rats were intragastrically given the test compound for 13 weeks and then recovered for 4 weeks, Compound I was given at a high dose of 30 mg/kg/day, steady-state $AUC_{0-24h}$ being about 49900 ng*h/mL. No obvious side effect was observed, and serum potassium level was not elevated.

ii. A Wide Safe Window was Observed in Heathy Volunteers

In one clinical trial, heathy volunteers were given a single dose of Compound I at a dose in the range of 0.5 to 30 mg/day. $AUC_{0-24h}$ was in the range of 162.5 to 5016 ng*h/mL, and no elevated serum potassium level was observed.

In another clinical trial, 6 heathy volunteers were given multiple administrations of Compound I at a dose of 5 mg/day. The average steady-state $AUC_{tau}$ was proved to be 6373±1026 ng*h/mL, and elevated serum potassium levels were observed in 3 subjects but were transient.

In a further clinical trial, Compound I was given to heathy volunteers at a dose of 2.5 mg/day in a multiple dosing manner. The average steady-state $AUC_{tau}$ was found to be 2863±822 ng*h/mL, and elevated serum potassium levels were not observed.

iii. A Very Narrow Safe Window was Found in Patients with Chronic Kidney Disease Patients having chronic kidney disease responded differently. When they were subject to multiple doses of Compound I at a dose of 2.5 mg/day, the safe steady-state $AUC_{tau}$ was 2613±280 ng*h/mL. In one subject, the serum potassium level slightly increased.

Pharmaceutical effects of Compound I was shown when patients having chronic kidney disease were given repeated doses of the compound at a dose of 0.5 mg/day. The average steady-state $AUC_{tau}$ was 652.5±232.2 ng*h/mL, and no elevated serum potassium level was observed.

In view of above, Compound I showed a wide safe window in the trials involving animals and heathy subjects but a very narrow safe window in patients with chronic kidney disease. The clinically safe window would be unpredictable from the animal or heathy people trials. In other words, the safe and effective window of Compound I in patients having chronic kidney disease is unpredictable.

In statistics, the 95% confidence interval in a normally distributed sample ranges from the mean minus twice the standard deviation to the mean plus twice the standard deviation. Based on the clinical trials mentioned above on CKD patients, the lower limit of AUC of Compound I showing effects in CKD patients administered with the pharmaceutical composition is determined to be the mean AUC minus twice the standard deviation measured at the dose of 0.5 mg, i.e., 188 ng*h/mL; and the upper limit of AUC of Compound I that is safe in CKD patients is the mean AUC plus twice the standard deviation measured at the dose of 2.5 mg, i.e., 3173 ng*h/mL; accordingly, the safe and effective AUC of Compound I is in the range of 188 ng*h/mL to 3173 ng*h/mL. Preferably, the lower limit of AUC of Compound I showing effects after absorbed by the patients is the mean AUC minus twice the standard deviation measured at the dose of 0.5 mg, i.e., 188 ng*h/mL, and the upper limit of AUC of Compound I that is safe in CKD patients is the mean AUC plus the standard deviation measured at the dose of 2.5 mg, i.e., 2893 ng*h/mL; accordingly, the safe and effective AUC of Compound I is in the range of 188 ng*h/mL to 2893 ng*h/mL. Preferably, the lower limit of AUC of Compound I showing effects after absorbed by the patients is the mean AUC minus twice the standard deviation measured at the dose of 0.5 mg, i.e., 188 ng*h/mL, and the upper limit of AUC of Compound I that is safe in CKD patients is the mean AUC measured at the dose of 2.5 mg, i.e., 2613 ng*h/mL; accordingly the safe and effective AUC of Compound I is in the range of 188 ng*h/mL to 2613 ng*h/mL. Preferably, the lower limit of AUC of Compound I showing effects after absorbed by the patients is the mean AUC minus twice the standard deviation measured at the dose of 0.5 mg, i.e., 188 ng*h/mL, and the upper limit of AUC of Compound I that is safe in CKD patients is the mean AUC plus twice the standard deviation measured at the dose of 0.5 mg, i.e., 1117 ng*h/mL; accordingly, the safe and effective AUC of Compound I is in the range of 188 ng*h/mL to 1117 ng*h/mL. Preferably, the lower limit of AUC of Compound I showing effects after absorbed by the patients is the mean AUC minus twice the standard deviation measured at the dose of 0.5 mg, i.e., 188 ng*h/mL, and the upper limit of AUC of Compound I that is safe in CKD patients is the mean AUC plus the standard deviation measured at the dose of 0.5 mg, i.e., 885 ng*h/mL; accordingly, the safe and effective AUC of Compound I is in the range of 188 ng*h/mL to 885 ng*h/mL.

In a pharmacodynamics experiment using salt-sensitive rats with renal injury induced by a high content of salts, the curve showing relationship between the change of SBP or UACR as compared to the baseline and $AUC_{0-24}$ (see FIG. 1 and FIG. 2) reveals an undulation point at 100 h*ng/mL of AUC after which the curve tends to be flat. It is indicated that the drug takes effect when AUC reaches 100 h*ng/mL.

In the first day when the CKD patients were administered at a dose of 0.5 mg/day, the steady-state $AUC_{tau}$ was found to be 105.6 h*ng/mL or more in these subjects, with UACR decreased by 30.5% or more compared to the baseline, suggesting the drug administration had taken effect.

The pharmacokinetic study on the group where multiple doses of Compound I were given at a dose of 0.5 mg/day was used to predict the steady-state $AUC_{tau}$ in other dosing groups. When the pharmaceutical composition with bioavailability of 50% in dogs was given to the CKD patients at a dose of 0.1 mg/day, the $AUC_{tau}$ was 130.5 h*ng/mL, which was above the lower limit of the effective $AUC_{tau}$ of 100 h*ng/mL, suggesting the drug administration at the dose of 0.1 mg/day had effects. That was, the daily dose of 0.1 mg took effect.

II. Enormous Individual Variation is Found Regarding Absorption of Compound I i. Big Individual Variation of Compound Absorption was Observed Individuals respond differently to a certain drug, which is called "individual variation of drug effect". For example, some people are not sensitive to a drug, and a standard dose may be not efficient to produce a therapeutic effect. On the other hand, some other people are particularly sensitive to the drug, and a very low dose may produce an obvious effect while a standard dose may cause an unusually intense effect, or even toxicity.

Further, drug absorption is also influenced by dietary conditions. For example, the drug absorption may be influenced by the fasting or bellyful state, or food composition. In the bellyful state, drug absorption will be retarded and the clearance rate will be slowed. The intake of water, tea, alcohol and high-fat food will also affect the absorption of the drug to some extent.

Compound I is insoluble in water and has a medium permeation rate. The patient's condition and diet will influence drug absorption. The pharmaceutical composition of this compound manufactured by conventional technical means provide low bioavailability, and enormous individual variation is observed in CKD patients. Studies have shown that the lower the bioavailability is, the bigger the individual variation will be. In the meanwhile, Compound I has a narrow safe window in patients having chronic kidney disease, posing a great safety risk on the application of this compound in these patients. Alcohol and high fat diet will particularly enhance the absorption of Compound I, further enlarging the individual variation and bring a bigger safety threat to the patients.

Thus, even if the clinical dose range is narrow, the bioavailability needs to be improved to reduce individual variation for the purpose of safe and effective clinic use of this compound.

Therefore, the safe and effective application of Compound I is closely related to the bioavailability and the dose of the pharmaceutical composition of the present invention.

ii. Effect of Compound I of Different Particle Sizes on Absorption a) For the sake of clinically safe and effective drug administration, the present inventors have found with extensive studies that the smaller the particle size of Compound I is, the higher the bioavailability will be when orally administered. The following sets forth the absorption of Compound I having different particle sizes in rats.

The bioavailability is 13.2%, when the particle-size distribution parameter $D_{90}$ of Compound I is 72.0 µm;

the bioavailability is 34.8%, when the particle-size distribution parameter $D_{90}$ of Compound I is 41.5 µm;

the bioavailability is 54.6%, when the particle-size distribution parameter $D_{90}$ of Compound I is 21.7 µm;

the bioavailability is 66.9%, when the particle-size distribution parameter $D_{90}$ of Compound I is 3.8 µm;

the bioavailability is 82.3%, when the particle-size distribution parameter $D_{90}$ of Compound I is 538 nm;

the bioavailability is 76.9%, when Compound I in the solid dispersion formulation is orally administered;

the bioavailability is 81.6%, when Compound I in the solution formulation is orally administered.

When manufactured by conventional means, Compound I has a $D_{90}$ of 72.2 µm. Its bioavailability is only 13.2% when orally given to rats. The bioavailability reaches 54.6% when $D_{90}$ is lowered to 21.7 µm. When Compound I is formulated as a solid dispersion or a solution, it is distributed as separate molecules, and its bioavailability will be 76.9% and 81.6%, respectively, when orally given to rats.

When Compound I has a $D_{90}$ of 25 µm or less, its availability is 50% or more, which meets the clinical safety and efficacy requirements.

b) Absorption of the Pharmaceutical Composition of the Present Invention in Dogs Capsule 5 as prepared in Example 2 was tested for its pharmacokinetic properties in Beagle dogs. The bioavailability was 50% or more when Compound I's $D_{90}$ was 5 µm, which met the clinical safety and efficacy requirements.

iii. Effect of the Surfactant on Absorption

In the pharmacokinetic study on rats, when no surfactant was used, the bioavailability was 34.8% with Compound I's $D_{90}$ being 41.5 µm. After sodium dodecyl sulfate (SDS) was added to Compound I as the surfactant in a ratio of 10:1 (SDS: Compound I), the bioavailability was 64.7% with Compound I's $D_{90}$ being 52.5 µm.

In the pharmacokinetic study on Beagle dogs using Capsule 5 prepared in Example 2 without any surfactant, the average bioavailability was 56.5%. When Tablet 3 prepared in Example 2 with sodium dodecyl sulfate (SDS), the bioavailability was proved to be 77.4%.

All these suggested that bioavailability can be greatly improved by adding a surfactant in the pharmaceutical formulation of the present invention, which may effectively reduce individual variation.

vi. Absorption of the Pharmaceutical Composition in Human Clinical Trials

The capsule prepared in Example 2 as a preferable embodiment (i.e., Capsule 5, having a $D_{90}$ of 5 µm and an average bioavailability of 56.5% in Beagle dogs) was used in the clinical trials.

In the clinical trials, the capsule of Compound I was administered with multiple doses at a daily dose of 2.5 mg. With respect to the AUC individual variation in heathy volunteers, the AUC in a subject having the highest AUC level was 2.37 times that of the subject with the lowest level. In CKD patients, AUC in a subject with the highest AUC level was 2.27 times that of the subject with the lowest.

In the clinical trials, the capsules of Compound I was also given to CKD patients in multiple doses at a daily dose of 0.5 mg. However, AUC in a subject with the highest AUC level was still 2.14 times that of the subject with the lowest level.

When formulated as described in the preferable embodiment of the present invention, Compound I had bioavailability of 56.5% in dogs. However, when such compound formulation was given to healthy subjects and CKD patients, AUC individual variation (AUC in the subject with the highest level being more than twice that of the subject having the lowest level) was still observed.

According to the above mentioned embodiments regarding the bioavailability of Compound I in mammals, the capsule prepared in Example 2 as a preferable embodiment had bioavailability of 50% or more in dogs. Then, this preferable capsule was administered in CKD patients in multiple doses at a daily dose of 0.5 mg or 2.5 mg, individual variation (AUC in the subject with the highest level being more than twice that of the subject having the lowest level) was observed. In addition to all these, Compound I was found to induce high serum potassium levels in CKD patients. Thus, it was determined that the bioavailability of 50% or more in mammals was a basic requirement, i.e., the bioavailability of 50% or more in the Beagle dogs was a must for the pharmaceutical composition of the present invention. The mentioned bioavailability requirement and the dose range in the present invention should be combined in consideration of safe and effective drug administration.

It was found with experiments that much too high AUC levels in some patients in relation to the individual variation problem can be avoided if the bioavailability of the pharmaceutical composition of the present invention can be increased to 50% or more in mammals. In this way, the risk of developing high serum potassium levels would be under control. For the safe and effective clinical drug application, the pharmaceutical composition of the present invention had its bioavailability in CKD patients increased, so as to reduce the individual variation and to secure the safety of drug use.

Bioavailability Improvement with Particle Size Decrease

In order to increase the bioavailability of the pharmaceutical composition of the present invention to a level of 50% or more in mammals, in one embodiment, the particle-size distribution parameter $D_{90}$ of Compound I is determined to be 25 µm or less. According to one embodiment of the present invention, the particle-size distribution parameter $D_{90}$ of Compound I is 21.7 µm or less. According to one embodiment of the present invention, the particle-size distribution parameter $D_{90}$ of Compound I is 10 µm or less.

According to one embodiment of the present invention, the particle-size distribution parameter $D_{90}$ of Compound I is 5 µm or less.

Compound I having different particle sizes may be prepared by means of grinding, extrusion, collision, cutting, mechanical pulverization, vibrational pulverization, fluid energy milling, ultra-sonication, high pressure grinding, chemical precipitation or the like.

Bioavailability Improvement with Addition of Surfactant

In order to increase the bioavailability of the pharmaceutical composition of the present invention to a level of 50% or more in mammals, in one embodiment, the pharmaceutical composition of the present invention contains a surfactant.

The surfactant is one or more selected from a group consisting of benzalkonium chloride, sodium lauryl sulfonate, sodium dodecyl sulfate, glycerol, cholic acid, poloxamer, polyvinyl alcohol, Polysorbate 80, PVP $K_{30}$ and Polyethylene glycol. Preferably, the surfactant is one or more selected from the group consisting of benzalkonium chloride, sodium lauryl sulfonate, and sodium dodecyl sulfate. Preferably, the surfactant is benzalkonium chloride, sodium lauryl sulfonate, or sodium dodecyl sulfate.

In the pharmaceutical composition of the present invention, the weight ratio of Compound I to the surfactant is 1:0.1 to 1:20, preferably 1:1 to 1:20, and more preferably 1:5 to 1:20.

Compound I of the present invention can be in any form. For example, Compound I can be in the amorphous, crystal or mixed crystal structure.

III. The Pharmaceutical Composition of the Present Invention has a Special Dose Range After the pharmaceutical composition of the present invention is administered, the AUC level of Compound I in humans is quite high, suggesting a considerably good drug efficacy. In clinical use, a very low dose will give a therapeutic effect.

The clinical doses of Spironolactone tablets and Eplerenone tables, two available mineralocorticoid receptor antagonists, are 40-400 mg/day and 25-50 mg/day, respectively. The doses are quite high.

In the trials of the pharmaceutical composition of the present invention, healthy volunteers were administered with a single dose of 0.5-30 mg, or alternatively administered in multiple doses at a daily dose of 2.5 mg, and showed very good tolerance. When the healthy volunteers were given in multiple doses at a dose of 5 mg/day, relatively good tolerance was also observed, despite one-off elevated serum potassium levels.

The pharmaceutical composition of the present invention, when given to the CKD patients in multiple doses at a daily dose of 0.5 mg, showed good therapeutic activity, with no elevated serum potassium levels being observed. When the pharmaceutical composition was administered in multiple doses at a dose of 2.5 mg/day, serum potassium fluctuation was found in one subject, indicating that no safety risk was posed on CKD patients at this dose.

In addition, it can be seen from the pharmacodynamics experiment using salt-sensitive rats with renal injury induced by a high content of salts as well as the clinical trial of the CKD patients that, the daily dose of 0.1 mg showed therapeutic effects on patients having chronic kidney disease.

The administration of the pharmaceutical composition of the present invention induces a very high AUC of Compound I in human bodies, indicating relatively good therapeutic activity. On the other hand, a very low dose of 0.1 mg in clinic use gives a therapeutic effect, meaning that the effective dose is quite low. Further, elevated serum potassium levels were not observed at the daily dose of 0.1 mg to 0.5 mg. As such, the dose range for the safe and effective use of the pharmaceutical composition of the present invention was finally found. The dose for the clinical use of the pharmaceutical composition of the present invention is unpredictable from the drugs available in markets or the clinical trial involving healthy volunteers.

In summary, Compound I may induce elevated serum potassium levels due to the underlying action mechanism of the mineralocorticoid receptor antagonist. The MRA drugs available in markets adopt very high clinical doses, and Compound I also shows a wide safe window in animal experiments and clinical trials where healthy volunteers are involved. Thus, it was assumed the clinical dose of Compound I would be quite high in patients having chronic kidney disease. However, in the clinical trials of the CKD patients, serum potassium levels were elevated at the daily dose of 2.5 mg, suggesting the dose range in CKD patients would be very narrow.

The inventors have found the safe and effective window for Compound I with lots of experiments. Further, base on the window, the dose range for the safe and effective use of the pharmaceutical composition of the present invention has been found. Also, the inventors have invented the pharmaceutical composition having bioavailability of 50% or more in mammals. When the patient having chronic kidney diseases is administered with the pharmaceutical composition of the present invention with the dose range disclosed herein, the AUC of Compound I is controlled at a safe and effective level, so that the safety and effectiveness of the clinical application is ensured.

Bioavailability is a measurement of the rate and extent to which a drug reaches the systemic circulation when administered via non-intravenous routes, and is an important parameter for assessment of drug absorption. Bioavailability includes absolute bioavailability and relative bioavailability, the former one comparing the absorption of the active drug following non-intravenous administration vs. intravenous administration, and latter one measuring the absorption of a formulation when compared with another formulation. The bioavailability herein refers to the absolute bioavailability.

The particle size herein may be also called grain size. In the pharmaceutical composition of the present invention, Compound I has a particle size of 100 µm or less, in the order of micron or nanometer, or existing as molecules.

The term $D_{90}$ herein refers to the size that splits the particle-size distribution with 10% above and 90% below this diameter.

The pharmaceutical composition of the present invention can effectively block the binding of the mineralocorticoid receptor to Aldosterone, and thus, according to the underlying action mechanism, can be specifically used in treatment and/or prevention of chronic kidney disease. The chronic kidney disease is selected from the group consisting of hypertensive nephropathy, diabetic nephropathy, glomerulonephritis, renal failure, albuminuria, kidney cyst, and glomerulosclerosis; chronic kidney disease with hypertension, chronic kidney disease with heart failure, chronic kidney disease with hypertension and heart failure, chronic kidney disease with obesity, chronic kidney disease with hyperlipoidemia, chronic kidney disease with diabetes mellitus, and cardiorenal syndrome; cardiovascular diseases selected from the group consisting of hypertension, heart failure (i.e., congestive heart failure, selected from the group consisting of heart failure with low ejection fraction, heart failure with normal ejection fraction, and acute heart failure), acute myocardial infarction, angina pectoris, cardiac hypertrophy, myocarditis, heart vascular fibrosis, myocardial ischemia, coronary atherosclerotic heart disease, coronary artery disease, baroreceptor dysfunction, fluid overload and cardiac arrhythmia, hyperlipoidemia and obesity; endocrine diseases selected from the group consisting of primary and secondary hyperaldosteronism, Addison's disease, Cushing's syndrome, and Bartter syndrome. In an embodiment, the present invention is also to the use of the pharmaceutical composition in preparation of medicaments for treatment of chronic kidney disease, heart failure and/or hypertension.

In another embodiment, the present invention provides a method for treating chronic kidney disease, heart failure and/or hypertension, comprising administering a subject in need thereof a therapeutically effective amount of the pharmaceutical composition of the present invention.

In an embodiment of the present invention, the pharmaceutical composition of the present invention may be administered once or for several times per day, preferably administered once with the dose as described above. The pharmaceutical composition of the present invention can be given at any time of the day.

The pharmaceutical composition of the present invention can be given to patients in need thereof in combination with other drugs which can be one or two selected from the group consisting of an antihypertensive agent, an antilipemic agent, and an antidiabetic agent.

The antihypertensive agent is selected from the group consisting of an angiotensin converting enzyme inhibitor, an angiotensin II receptor blocker, a renin inhibitor, a calcium channel blocker, a diuretic, a beta-receptor blocker, and an alpha-receptor blocker. Specifically, the antihypertensive agent includes, but not limited to, the angiotensin converting enzyme inhibitor, selected from the group consisting of Captopril, Enalapril, Benazepril, Delapril, Lisinopril, and Perindopril; the angiotensin II receptor blocker, selected from the group consisting of Losartan, Valsartan, irbesartan, Candesartan, Telmisartan, Eprosartan, and Irbesartan; the renin inhibitor, selected from the group consisting of Aliskiren and Aliskiren; the calcium channel blocker, selected from the group consisting of Nifedipine, Amlodipine, Lercanidipine, Nimodipine, Nicardipine, Nitrendipine, Nisoldipine, Felodipine, Benidipine, Lacidipine, Diltiazem, Verapamil, Flunarizine, Cinnarizine, and Lidoflazine; the diuretic, selected from the group consisting of chlorothiazide, Chlortralidone, and Furosemide; the beta-receptor blocker, selected from the group consisting of Atenolol, Metoprolol, Sotaol hydrochloride, Propranolol Hydrochloride, and Carvedilol; and the alpha-receptor blocker, selected from the group consisting of Phentolamine, Tolazoline, Phenoxybenzamine, and Prazosin; the antilipemic agent, selected from the group consisting of Atorvastatin, Lovastatin, Simvastatin, Pravastatin, fluvastatin, Rosuvastatin, Ciprofibrate, Bezafibrate, Fenofibrate, and Gemfibrozil The antilipemic agent is selected from the group consisting of Atorvastatin, Lovastatin, Simvastatin, Pravastatin, fluvastatin, Rosuvastatin, Ciprofibrate, Bezafibrate, Fenofibrate, and Gemfibrozil.

The antidiabetic agent is selected from the group consisting of an insulinotropic agent, metformins, an α-glucosidase inhibitor, a thiazolidinedione derived sensitizing agent, a Meglitinides derived insulinotropic agent, a GLP-1 receptor agonist, and a DPP-4 inhibitor. The antidiabetic agent includes, but not limited to, a sulfonylureas insulinotropic agent, selected from the group consisting of Glipizide, Gliclazide, Glibenclamide, Glibornuride, Glimepiride, and Gliquidone; a non-sulfonylureas Meglitinides derived insulinotropic agent, selected from the group consisting of Repaglinide and Nateglinide; metformins, selected from metformin; an alpha-glucosidase inhibitor, selected from the group consisting of Bose-100, Acarbose, and Voglibose; an insulin sensitizing agent, selected from Rosiglitazone, and Pioglitazone; a dipeptidyl peptidase 4 (DPP-4) inhibitor, selected from the group consisting of Sitagliptin, Saxagliptin, and Vildagliptin; and a GLP-1 receptor agonist, selected from Exenatide, and Liraglutide.

The pharmaceutical composition of the present invention contains Compound I and a pharmaceutically acceptable carrier, and can be administered via appropriate routes, including but not limited to, oral, parenteral, intraperitoneal, intravenous, transdermal, sublingual, intramuscular, rectal, nasal, and subcutaneous administrations.

The pharmaceutical composition of the present invention is preferably an oral formulation, and more preferably tablets, extended-release tablets, capsules, or granules. The pharmaceutical composition of the present invention can also be soft capsules, dripping pills, micro-capsules, microspheres, liposomes, a self-emulsifying drug delivery system, solid dispersions, micelles, oral melt tablets, solutions, suspensions, or emulsions.

The pharmaceutically acceptable carrier in the pharmaceutical composition of the present invention is one or more non-toxic pharmaceutical carriers. These carriers may be compatible with other ingredients in the pharmaceutical composition, and do no harm to the subjects taking the composition.

Carriers

The pharmaceutical composition of the present invention is prepared as an oral formulation and comprises one or more carriers, including diluents, fillers, lubricants, glidants, binders, disintegrating agents, surfactants, and the like. The carriers used in the pharmaceutical composition of the present invention can be selected and combined to provide better properties, generating safe, effective and controllable pharmacokinetics when the composition is administered to the subject, and meeting the drug administration requirements.

The diluent or filler, used to increase the weight of a single-dose formulation, includes, but not limited to, calcium phosphate, calcium sulfate, microcrystalline cellulose, lactose, mannitol, sorbitol, starch and the like.

The lubricant, used to reduce the friction between the granules and the mold wall upon compression or discharge, to prevent the granules from attaching to the tablet punching machine, and/or to discharge the granules out of the tablet punching machine, includes, but not limited to, talc, stearic acid, calcium stearate, zinc stearate, magnesium stearate, vegetable oils and the like.

The glidant, added to improve the fluidity of the granules, includes, but not limited to, talc, silicon dioxide and corn starch.

The binder includes, but not limited to, pyrrolidone, polyvinyl pyrrolidone, xanthan gum, cellulose gum (such as carboxymethyl cellulose, methyl cellulose, hydroxyethyl cellulose, hydroxypropyl cellulose, hydroxypropyl methyl cellulose), gelatin, and starch.

The disintegrating agent, with which the tablets can quickly fragment into small particles in the gastrointestinal fluid so that the active gradients will be dissolved and absorbed to exert effects, includes, but not limited to, starch, clay, cellulose, alginates, pregelatinized starch, crospolyvinylpyrrolidone, croscarmellose sodium, carboxymethyl starch sodium, vegetable glue, and the like.

The surfactant, capable of altering the interfacial tension to provide moistening and solubilizing effects, includes, but not limited to, poloxamer, sodium dodecyl sulfate, polysorbates, polyethylene glycol octanoate, glyceryl caprate, polyethylene glycol glyceryl laurate, polyethylene glycol glyceryl stearate, and the like.

Other carrier materials include, but not limited to, preservatives, antioxidants, and other carrier materials commonly used in pharmaceutical industry.

The extended-release tablets may contain one or more carrier materials selected from the group consisting of cellulose ether derivatives, including hydroxypropyl methyl cellulose, ethyl cellulose, sodium carboxymethyl cellulose, and hydropropyl cellulose; acrylic polymers, including Carbomer, and acrylic resin; chitin and the derivatives, polylactic acid, and the like. Other additives may be further added, the common ones including wetting agents (such as ethanol, water, and the like), colorants (such as ferric oxides), preservatives, antioxidants, anti-collapse agents (such as glycine), surfactants (such as sodium dodecyl sulfate), pH regulators (such as sodium citrate or sodium hydroxide), fillers (microcrystalline cellulose and the like), and disintegrating agents (croscarmellose sodium and the like).

The commonly used additives for the solution formulation, such as the oral formulation of the present invention, include those for flavor improvement, for clarity improvement, and for stability enhancement. The additive for flavor improvement usually includes four classes, i.e., the sweetener, aromatics, mucilage, and effervescent agent. The sweetener contains naturally occurring and artificially made ones. The naturally occurring sweetener can be sucrose, simple syrup, and syrupus aromaticus, while the artificial one can be saccharin sodium, aspartame, and the like. The aromatics includes the lemon extract, the peppermint oil, the apple essence and the rubber essence. The commonly used mucilage can be sodium alginate, Arabic gum, gelatin, methyl cellulose, sodium carboxymethyl cellulose and the like. The effervescent agent can be citric acid, tartaric acid, and the like. The additive for clarity enhancement is, for example, chitosan, 101 juice clarifying agent, ZTC1+1 naturally occurring clarifying agent, gelatin, tannic acid, egg whites, and the like. The additive for enhancing stability can be parahydroxybenzoate esters, organic acids and salts thereof, and others such as chlorhexidine di(acetate), domiphen, and the like.

The common additives for the soft capsules can be vegetable oils, aromatic esters, organic acids, glycerol, isopropanol, polyethylene glycol, propanediol, and surfactants.

The dripping pills may contain one or more base materials selected from the group consisting of the water-soluble base, the water-insoluble base, and the mixed base. The water-soluble based mainly includes Polyethylene glycol 4000, Polyethylene glycol 6000, polyvinyl pyrrolidone (PVP), S-40 (Polyoxyethylene monostearate), sodium stearate, glycerol, gelatin, urea, poloxamer, PEG plus surfactants, and polyethers. The main water-insoluble bases are stearic acid, glyceryle monostearate, the insect wax, hydrogenated vegetable oils, stearyl alcohol, cetyl alcohol, and semi-synthetic fatty acids. The mixed base can be, for example, polyethylene glycol plus S-40 or poloxamer. The mixed based is employed for the purpose of increasing the amount of the drug to be distributed, adjusting the distribution time limit or disintegration time limit, which may be helpful for the formulation of dripping pills.

The suspensions may contain one or more carrier materials selected from the group consisting of the suspending agent, the wetting agent, the flocculating agent, and the de-flocculating agent.

The frequently used suspending agents include, but not limited to, suspending agents of small molecules such as glycerol and syrups; and polymers such as 1) the naturally occurring polymer which is mainly the vegetable glue such as Arabic gum, gummi tragacanthae, and peach gum, and the vegetable polysaccharide such as sodium alginate, agar, and starch paste; 2) synthetic or semi-synthetic polymers, including celluloses such as methyl cellulose, sodium carboxymethyl cellulose, and hydropropyl cellulose, and others such as carbopol, povidone, and glucan; 3) diatomaceous earth; and 4) thixotrope.

The wetting agent includes, but not limited to, polysorbates, polyoxyethylene castor oil, and poloxamer.

The flocculating agent includes, but not limited to, inorganic flocculating agents such as aluminium sulfate, aluminium chloride, ferric sulfate, and ferric chloride; modified mono-cationic inorganic flocculating agents such as polysilicate aluminum (ferrite), and polyphosphate aluminum (ferrite); modified poly-cationic inorganic flocculating agents such as polyferric aluminum chloride sulfate, polyferric silicate, ferric-aluminum copolymer and the like; organic polymers such as polyacrylamide; composite flocculating agents such as polyaluminium chloride and polyferric sulfate; and microbial flocculating agents such as Phodococcus *erythropolis* and NOC-1 containing the same.

The de-flocculating agent includes, but not limited to, sodium citrate, tartrates, phosphates, carbonates, glycinates, magnesium succinate, and sodium dehydrocholate.

The micro-capsules may contain one or more carrier materials selected from the group consisting of gelatin, Arabic gum, albumin, starch, chitosan, alginates, methyl cellulose, ethyl cellulose, carboxymethyl cellulose, hydropropyl methyl cellulose, polylactic acid, poly lactic-coglycolic acid, polyalkylcyanoacrylate, polyamide, poly(vinyl alcohol), and polyacrlic resin.

The micro-spheres may contain one or more carrier materials selected from the group consisting of naturally occurring polymeric micro-spheres, such as starch microspheres, albumin micro-spheres, gelatin micro-spheres, chitosans and the like; and synthetic polymeric micro-spheres such as polylactic acid micro-spheres and the like.

The liposomes may comprise one or more carrier materials selected from the group consisting of phospholipids and cholesterols. The phospholipids include the naturally occurring and synthetic ones. The main naturally occurring phospholipid is lecithin (phosphatidyl choline, PC), while the synthetic phospholipid is mainly DPPC (dipalmitoyl phosphatidylcholine), DPPE (Dipalmitoyl Phosphoethanolamin) and DSPC (distearoyl phosphatidylcholine).

The self-emulsifying drug delivery system may contain one or more selected from the group consisting of oils, surfactants and co-surfactants.

The oils are divided into the naturally occurring vegetable oils (such as soy oil, peanut oil and the like), medium chain triglycerides, and semi-synthetic medium chain derivatives such as coconut oil C8/C10 triglycerides, coconut oil C8/C10 monoglycerides or diglycerides, sorbitan oleate, glyceryl oleate-propylene glycol, glyceryl oleate, propylene glycol monooctoate, glyceryl tributyrate, and purified acetylated monoglycerides.

The surfactants are mainly polyoxyethylene castor oil, polyoxyethylene hydrogenated castor oil, polyoxyethylene sorbitan oleate, polyoxyethylene triglycerides, PEG-8 caprylic/capric glycerides, coconut oil C8/C10 polyglycolized glycerides, polyethylene glycol lauric glyceride, Labrafil M 1944CS and Lavrafil M-22125CS.

Co-surfactants include, but not limited to, ethanol, propylene glycol, glycerol, isopropanol, polyethylene glycol, and propenyl ethylene glycol laurate.

There are three types of carrier materials for the solid dispersions. They are water-soluble carrier materials, including polyethylene glycol (PEG), polyvinyl pyrrolidone (PVP), surfactants, organic acids, saccharides, alcohols, and the like; insoluble carrier materials, including cellulose, and polyacrylic resin; and enteric materials, including cellulose, and polyacrylic resins.

The micelles contain surfactants, including but not limited to, hexadecyl trimethyl ammonium chloride, hexadecyl trimethyl ammonium bromide, dodecyl trimethyl aminium bromide, dodecylpyridinium bromide, sodium octanesulfonate, sodium octyl sulfate, sodium dodecyl sulfate, sodium tetradecyl sulfate, sodium hexadecyl sulfate, sodium octadecyl sulfate, potassium stearate, potassium oleate, potassium laurate, sodium dodecylsulfonate, polyoxyethylene(6) lauryl ether, polyoxyethylene(9) lauryl ether, polyoxyethylene(12) lauryl ether, polyoxyethylene(6) myristyl ether, dioctyl sodium sulfosuccinate, dodecyl ammonium chloride, sodium dodecyl benzene sulfonate, sucrose laurate, sucrose palmitate, sucrose stearate, Tween-20, Tween-40, Tween-60, Tween-65, Tween 80, and Tween 85.

The oral melt tablets may contain one or more materials selected from the group consisting of surfactants, such as sodium dodecyl sulfate, lecithin, Tween, and Span; long-chain polymers, such as polypeptides (gelatin or dehydrated gelatin); saccharides and derivatives, such as dextran, glucans, sorbitol, mannitol, and starch; gels, such as Arabic gum, xanthan gum, and vegetable glue; celluloses; alginates; PVP; and polyvinyl alcohol. Some other additives may be added, including the wetting agent (such as ethanol), the colorant (such as ferric oxides), the preservative, the antioxidant, the anti-collapse agent (such as glycine), the penetration enhancer (such as sodium dodecyl sulfate), the pH regulator (such as sodium citrate or sodium hydroxide), the aromatics, and the sweetener.

DETAILED DESCRIPTION OF THE INVENTION

Figure 1:
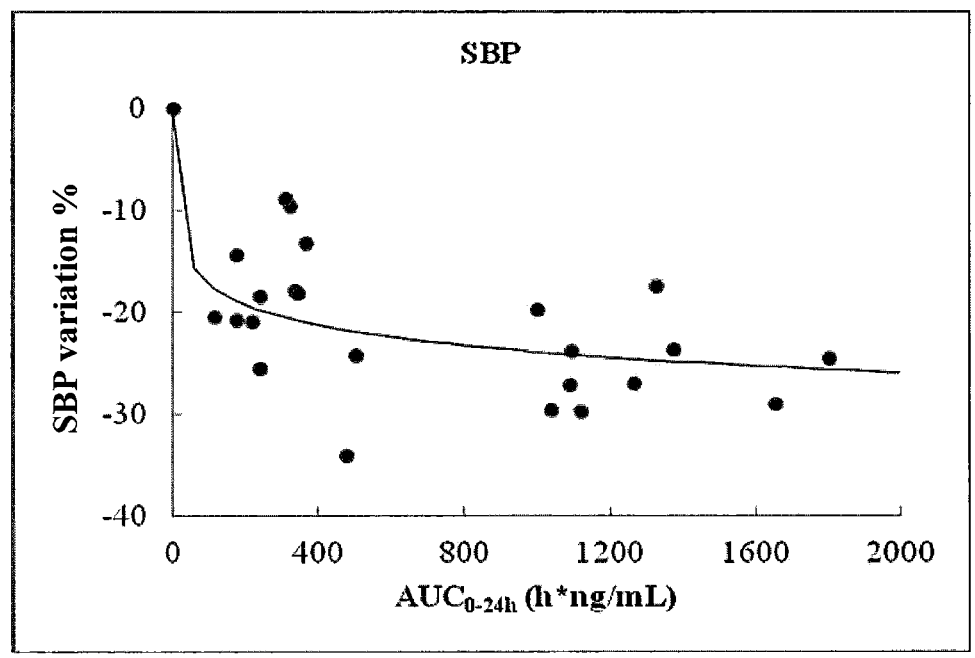
FIG. 1 is a curve showing the correlation between SBP variation based on baselines and $AUC_{0-24}$ in a DSS rat model with hypertension and renal injury induced by a high content of salts.

The present invention includes, but not limited to, the following examples. Other embodiments for carrying out the technical solution of the present invention fall within the scopes as claimed in the present invention.

Example 1. Preparation of Compound I 2-chloro-4-[(3S,3aR)-3-cyclopentyl-7-(4-hydroxylpiperidine-1-carbonyl)-3,3a,4,5-tetrahydro-2H-pyrazolo[3,4-f]quinolin-2-yl]benzonitrile (herein referred to as "Compound I"), with the structure as shown below.

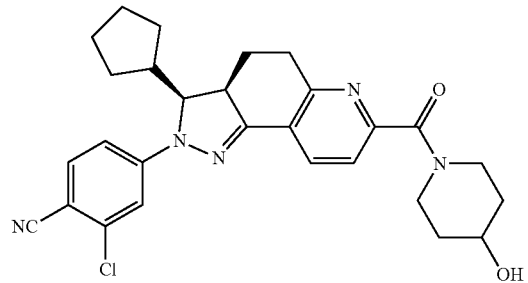

Compound I

Compound I may be prepared by the method described in WO2012022121A1 or WO2014094664A1, or other synthesis methods.

Example 2. Exemplary Formulations of the Pharmaceutical Composition of the Present Invention The examples of the present invention present part of the formulations of the pharmaceutical composition, which are used for the administration of the pharmaceutical composition of the present invention. It should be noted that the formulation herein is not limited to the following ones, other formulations having bioavailability of 50% or more fall within the scopes of the present invention as claimed.

Exemplary tablet formulations are shown below.

Formulation 1. Each tablet contained 0.5 mg of Compound I.

| | |
|---|---|
| Compound I having $D_{90}$ of 538 nm | 0.5 g of $C_{28}H_{30}ClN_5O_2$ |
| Microcrystalline cellulose PH101 | 30 g |
| Mannitol | 70 g |
| Croscarmellose Sodium | 6 g |
| Polyvinyl pyrrolidone K30 | 2.15 g |
| Magnesium stearate | 2 g |
| Silicon dioxide | 2 g |
| Formulated into | 1000 tablets |

Manufacturing Process:

(1) Polyvinylpyrrolidone K30 was formulated into an aqueous solution with a concentration of 5% (w/w), to be used as the binder;

(2) Microcrystalline cellulose PH101, mannitol, and Croscarmellose Sodium were weighed in amounts as described above and sufficiently mixed for 15 minutes to obtain Mixture 1;

(3) Suspension containing 0.5 g of nanosized Compound I was weighed, and then added into and mixed with Mixture 1; the resultant mixture was added with the aqueous solution of Polyvinylpyrrolidone K30, the binder, to obtain soft material, which was treated by a 24-mesh screen to make wet granules;

(4) The wet granules were dried at 55±5° C. for 2 to 3 hours, the granules' water content being controlled at a level below 2.5%;

(5) The dried granules were screened by the 24-mesh screen again;

(6) Magnesium stearate and Silicon dioxide were added to the granules at amounts described above and then mixed for 15 minutes;

(7) Tablet compression was done, with tablet hardness controlled at 6 to 10 kg;

(8) Tablets were coated;

(9) Tablets were packaged and warehoused.

Formulation 2. Each tablet contained 0.5 mg of Compound I.

| | |
|---|---|
| Compound I having $D_{90}$ of 4.0 μm | 0.5 g of $C_{28}H_{30}ClN_5O_2$ |
| Sodium dodecyl sulfate | 5 g |
| Microcrystalline cellulose PH101 | 40 g |
| Lactose monohydrate | 60 g |
| Croscarmellose Sodium | 3.5 g |
| Hydroxypropyl cellulose | 5 g |
| Magnesium stearate | 2.0 g |
| Silicon dioxide | 1.0 g |
| Formulated into | 1000 tablets |

Formulation 3. Each tablet contained 2.5 mg of Compound I.

| | |
|---|---|
| Compound I having $D_{90}$ of 4.0 μm | 2.5 g of $C_{28}H_{30}ClN_5O_2$ |
| Sodium dodecyl sulfate | 25 g |
| Microcrystalline cellulose PH101 | 40 g |
| Lactose monohydrate | 60 g |
| Croscarmellose Sodium | 3.5 g |
| Hydroxypropyl cellulose | 5 g |
| Magnesium stearate | 2.0 g |
| Silicon dioxide | 1.0 g |
| Formulated into | 1000 tablets |

Manufacturing Process:
(1) The starting materials were screened by a 30-mesh screen and stored for further use;
(2) Compound I, sodium dodecyl sulfate, microcrystalline cellulose PH101, lactose monohydrate, Croscarmellose Sodium and hydroxypropyl cellulose were sufficiently mixed for 15 minutes;
(3) Water was added into the mixture to obtain soft material which was treated by a 24-mesh screen to make wet granules;
(4) The wet granules were dried at 55±5° C. for 2 to 3 hours, the granules' water content being controlled at a level below 2.5%;
(5) The dried granules were screened by the 24-mesh screen again;
(6) Magnesium stearate and silicon dioxide were added to the granules at amounts described above and then mixed for 15 minutes;
(7) Tablet compression was done, with tablet hardness controlled at 6 to 10 kg;
(8) Tablets were coated;
(9) Tablets were packaged and warehoused.

Exemplary capsule formulations are shown below.

Formulation 1. Each capsule contained 0.1 mg of Compound I.

| | |
|---|---|
| Compound I having $D_{90}$ of 5 μm | 0.1 g of $C_{28}H_{30}ClN_5O_2$ |
| Microcrystalline cellulose PH101 | 30.0 g |
| Mannitol | 70.0 g |
| Croscarmellose Sodium | 6.0 g |
| Polyvinylpyrrolidone K30 | 2.15 g |
| Magnesium stearate | 2.0 g |
| Silicon dioxide | 2.0 g |
| Formulated into | 1000 capsules |

Formulation 2. Each capsule contained 0.25 mg of Compound I.

| | |
|---|---|
| Compound I having $D_{90}$ of 5 μm | 0.25 g of $C_{28}H_{30}ClN_5O_2$ |
| Microcrystalline cellulose PH101 | 30.0 g |
| Mannitol | 70.0 g |
| Croscarmellose Sodium | 6.0 g |
| Polyvinylpyrrolidone K30 | 2.15 g |
| Magnesium stearate | 2.0 g |
| Silicon dioxide | 2.0 g |
| Formulated into | 1000 capsules |

Manufacturing Process:
(1) Polyvinylpyrrolidone K30 was formulated into an aqueous solution with a concentration of 5% (w/w), to be used as the binder;
(2) Compound I, microcrystalline cellulose PH101, mannitol, and Croscarmellose Sodium were weighed in amounts described above and sufficiently mixed for 15 minutes; water content of the obtained mixture was measured;
(3) The resultant mixture was added with the aqueous solution of Polyvinylpyrrolidone $K_{30}$ as the binder to obtain soft material, which was treated by a 24-mesh screen to make wet granules; (4) The wet granules were dried at 55±5° C. for 2 to 3 hours, the granules' water content being controlled at a level below 2.5%;
(5) The dried granules were screened by the 24-mesh screen again;
(6) Magnesium stearate and Silicon dioxide were added to the granules at amounts described above and then mixed for 15 minutes;
(7) The amount of the obtained mixture to be inserted into the capsule was calculated and the mixture was weighed at this amount and put into the capsule;
(8) Capsules were put into bottles made of high-density polyethylene for oral solid drugs, and the bottles were sealed;
(9) The bottles were warehoused.

Formulation 3. Each capsule contained 0.5 mg of Compound I.

| | |
|---|---|
| Compound I having $D_{90}$ of 5 μm | 0.5 g of $C_{28}H_{30}ClN_5O_2$ |
| Microcrystalline cellulose PH101 | 30.0 g |
| Mannitol | 70.0 g |
| Croscarmellose Sodium | 6.0 g |
| Polyvinylpyrrolidone K30 | 2.15 g |
| Magnesium stearate | 2.0 g |
| Silicon dioxide | 2.0 g |
| Formulated into | 1000 capsules |

Formulation 4. Each capsule contained 2.5 mg of Compound I.

| | |
|---|---|
| Compound I having $D_{90}$ of 5 μm | 2.5 g of $C_{28}H_{30}ClN_5O_2$ |
| Microcrystalline cellulose PH101 | 30.0 g |
| Mannitol | 70.0 g |
| Croscarmellose Sodium | 6.0 g |
| Polyvinylpyrrolidone K30 | 2.15 g |
| Magnesium stearate | 2.0 g |
| Silicon dioxide | 2.0 g |
| Formulated into | 1000 capsules |

Formulation 5. Each capsule contained 10 mg of Compound I.

| | |
|---|---|
| Compound I having $D_{90}$ of 5 μm | 10 g of $C_{28}H_{30}ClN_5O_2$ |
| Microcrystalline cellulose PH101 | 30.0 g |
| Mannitol | 70.0 g |
| Croscarmellose Sodium | 6.0 g |
| Polyvinylpyrrolidone K30 | 2.15 g |

| | |
|---|---|
| Magnesium stearate | 2.0 g |
| Silicon dioxide | 2.0 g |
| Formulated into | 1000 capsules |

Manufacturing Process:

(1) Preparation of the binder solution: Polyvinylpyrrolidone K30 was formulated into an aqueous solution with a concentration of 3 to 5% (w/w), to be used as the binder;

(2) Mixing: Microcrystalline cellulose PH101, mannitol, and Croscarmellose Sodium were passed through a 30-mesh screen and then transferred with Compound I to a high-shear granulation machine where they were mixed for 2 to 3 minutes at an agitating speed of 180 to 220 r/min and a cutting speed of 475 to 525 r/min;

(3) Granulation: The binder solution was added to the mixture obtained in step (2) within 5 to 7 minutes after the completion of step (2), and the mixture was subject to granulation at an agitating speed of 180 to 220 r/min and a cutting speed of 475 to 525 r/min, followed by granulation for 0.5 to 1.5 minutes at an agitating speed of 180 to 220 r/min and a cutting speed of 1800 to 2200 r/min;

(4) Drying: The wet granules were dried at 55±5, the granules' water content being controlled at a level below 2.5%;

(5) Breaking: The dried granules were put into Fitz Mill and forced through Screen #0033 at a rotating speed of 840 to 960 r/min; the breaking step can be performed using other methods or devices as long as the same effect can be produced;

(6) Mixing: Magnesium stearate and Silicon dioxide were screened, respectively, using the 30-mesh screen or some other devices; the silicone dioxide was then put into a V-shaped mixer and mixed for 12 minutes at 20 r/min; magnesium stearate was added to and mixed with the silicone dioxide for 3 minutes at 20 r/min;

(7) Capsule filling: The mixed powder was filled into capsules using a capsule filling machine (MF-30);

(8) Polishing: The capsules were polished using a capsule polishing machine;

(9) Packing and labeling: The capsules were put into HDPE bottles whose caps were screwed tight and sealed using an electromagnetic sealing machine; bottles were labeled later.

Formulation 6. Each capsule contained 2.5 mg of Compound I.

| | |
|---|---|
| Compound I having $D_{90}$ of 21.7 μm | 2.5 g of $C_{28}H_{30}ClN_5O_2$ |
| Microcrystalline cellulose PH101 | 40.0 g |
| Lactose monohydrate | 60.0 g |
| Croscarmellose Sodium | 3.0 g |
| Magnesium stearate | 2.0 g |
| Silicon dioxide | 2.0 g |
| Formulated into | 1000 capsules |

Manufacturing Process:

(1) The starting materials were passed through a 30-mesh screen and stored for future use;

(2) Mixing: Compound I, microcrystalline cellulose PH101, lactose monohydrate, Croscarmellose Sodium, magnesium stearate and silicon dioxide were evenly mixed for 15 minutes;

(3) The amount to be inserted into the capsule was calculated, and the mixture at the amount was put into the capsules;

(4) The capsules were put into bottles made of high-density polyethylene for oral solid drugs, and the bottles were sealed;

(5) The bottles were warehoused.

The exemplary self-emulsifying drug delivery system (SEDDS) is shown below.

SEDDS Formulation

CompoundI:ethanol:Kolliphor EL:Miglyol 812N=10 mg:1 g:5 g:4 g

Manufacturing Process:

Compound I was dissolved in ethanol, which was added and mixed with Kolliphor EL and Miglyol 812N to obtain an emulsified mixture.

Exemplary soft capsule formulations are shown below.

Formulation 1. Each soft capsule contained 0.25 mg of Compound I.

| | |
|---|---|
| Compound I | 0.25 g of $C_{28}H_{30}ClN_5O_2$ |
| Polyethylene glycol 400 | 240 g |
| Propylene glycol | 30 g |
| Formulated into | 1000 capsules |

Formulation 2. Each soft capsule contained 0.5 mg of Compound I.

| | |
|---|---|
| Compound I | 0.5 g of $C_{28}H_{30}ClN_5O_2$ |
| Polyethylene glycol 400 | 240 g |
| Propylene glycol | 30 g |
| Formulated into | 1000 capsules |

Formulation 3. Each soft capsule contained 1.0 mg of Compound I.

| | |
|---|---|
| Compound I | 1.0 g of $C_{28}H_{30}ClN_5O_2$ |
| Polyethylene glycol 400 | 240 g |
| Propylene glycol | 30 g |
| Formulated into | 1000 capsules |

Manufacturing Process:

(1) Compound I was mixed with and dissolved in polyethylene glycol 400 and propylene glycol;

(2) The mixture was pressed into soft capsules;

(3) The soft capsules were packaged and warehoused.

Exemplary suspension formulations are shown below.

Formulation 1. The suspension contained 0.25 mg of Compound I per milliliter.

| | |
|---|---|
| Compound I | 0.25 g of $C_{28}H_{30}ClN_5O_2$ |
| Methyl cellulose | 5 g |
| Water added to | 1000 mL |
| Formulated into | 1000 mL |

Manufacturing Process:

(1) Methyl cellulose was dissolved in water whose amount was about 80% of that totally used; the solution was kept for future use;

(2) Compound I was weighed and put into the solution; after sufficient mixing, Compound I was suspended in the solution;

(3) Water was added to a total volume of 1000 mL, and sufficient mixing was done.

Formulation 2 The suspension contained 0.5 mg of Compound I per milliliter.

| Compound I | 0.5 g of $C_{28}H_{30}ClN_5O_2$ |
|---|---|
| Methyl cellulose | 5 g |
| Water added to | 1000 mL |
| Formulated into | 1000 mL |

Formulation 3. The suspension contained 1.0 mg of Compound I per milliliter.

| Compound I | 1.0 g of $C_{28}H_{30}ClN_5O_2$ |
|---|---|
| Methyl cellulose | 5 g |
| Water added to | 1000 mL |
| Formulated into | 1000 mL |

Exemplary emulsion formulations are shown below.

Formulation 1. The emulsion contained 0.25 mg of Compound I per milliliter.

| Compound I | 0.25 g of $C_{28}H_{30}ClN_5O_2$ |
|---|---|
| Polyethylene glycol 400 | 50 g |
| Span 80 (Sorbitan oleate) | 3 g |
| Tween 80 | 6 g |
| Soybean oil | 50 g |
| Glyceryl Monostearate | 10 g |
| Water added to | 1000 mL |
| Formulated into | 1000 mL |

Manufacturing Process:
(1) Water phase preparation: Compound I and polyethylene glycol 400 were heated to 60° C. so that Compound I was dissolved; the solution was kept warm for future use;
(2) Oil phase preparation: Glyceryl Monostearate and soybean oil were heated to 60° C. and dissolved; the solution was kept warm for future use;
(3) The water phase was added to and mixed at 60° C. with the oil phase, and the resultant mixture was added with and mixed at 60° C. with Span 80 and Tween 80; water was added to a total volume of 1000 mL; the obtained mixture was ground into uniform size using a colloid mill.

Formulation 2. The emulsion contained 0.5 mg of Compound I per milliliter.

| Compound I | 0.5 g of $C_{28}H_{30}ClN_5O_2$ |
|---|---|
| Polyethylene glycol 400 | 50 g |
| Span 80 | 3 g |
| Tween 80 | 6 g |
| Soybean oil | 50 g |
| Glyceryl Monostearate | 10 g |
| Water added to | 1000 mL |
| Formulated into | 1000 mL |

Formulation 3. The emulsion contained 1.0 mg of Compound I per milliliter.

| Compound I | 1.0 g of $C_{28}H_{30}ClN_5O_2$ |
|---|---|
| Polyethylene glycol 400 | 50 g |
| Span 80 | 3 g |
| Tween 80 | 6 g |
| Soybean oil | 50 g |
| Glyceryl Monostearate | 10 g |
| Water added to | 1000 mL |
| Formulated into | 1000 mL |

Exemplary dripping pill formulations are shown below.

Formulation 1. Each pill contained 0.1 mg of Compound I.

| Compound I having $D_{90}$ of 5 μm | 0.1 g of $C_{28}H_{30}ClN_5O_2$ |
|---|---|
| Polyethylene glycol 4000 | 60.0 g |
| Polyethylene glycol 6000 | 30.0 g |
| Formulated into | 1000 pills |

Formulation 2. Each pill contained 0.25 mg of Compound I.

| Compound I having $D_{90}$ of 5 μm | 0.25 g of $C_{28}H_{30}ClN_5O_2$ |
|---|---|
| Polyethylene glycol 4000 | 60.0 g |
| Polyethylene glycol 6000 | 30.0 g |
| Formulated into | 1000 pills |

Formulation 3. Each pill contained 0.5 mg of Compound I.

| Compound I having $D_{90}$ of 5 μm | 0.5 g of $C_{28}H_{30}ClN_5O_2$ |
|---|---|
| Polyethylene glycol 4000 | 60.0 g |
| Polyethylene glycol 6000 | 30.0 g |
| Formulated into | 1000 pills |

Formulation 4. Each pill contained 1.0 mg of Compound I.

| Compound I having $D_{90}$ of 5 μm | 1.0 g of $C_{28}H_{30}ClN_5O_2$ |
|---|---|
| Polyethylene glycol 4000 | 60.0 g |
| Polyethylene glycol 6000 | 30.0 g |
| Formulated into | 1000 pills |

Manufacturing Process:
(1) Compound I, polyethylene glycol 4000 and polyethylene glycol 6000 were weighted at the amounts set forth above for future use;
(2) Polyethylene glycol 4000 and polyethylene glycol 6000 were melted with a water bath at 80° C., and then added with Compound I which was dissolved with stirring; the mixture was kept at 80° C. for future use;
(3) At the temperature of 80° C., the mixture was added dropwise into condensed dimethicone where the mixture was condensed as solid pills;
(4) The pills were fetched out and drained dry, and then put into polyethylene bottles which were properly sealed.

Exemplary oral melt tablet formulations are shown below.

Formulation 1. Each oral melt tablet contained 0.25 mg of Compound I.

| Compound I | 0.25 g of $C_{28}H_{30}ClN_5O_2$ |
|---|---|
| Microcrystalline cellulose PH101 | 10 g |
| Mannitol | 80 g |
| Croscarmellose Sodium | 10 g |
| Water | q.s. |
| Magnesium stearate | 1.0 g |
| Silicon dioxide | 1.0 g |
| Formulated into | 1000 tablets |

Manufacturing Process:
(1) Compound I, microcrystalline cellulose PH101, mannitol and Croscarmellose Sodium were evenly mixed;
(2) Water was added to the mixture to perform granulation, and the obtained granules were dried;
(3) Magnesium stearate and silicon dioxide were added to be uniformly mixed with granules;
(4) Pelleting was done;
(5) The obtained tablets were coated and then packaged.

Formulation 2. Each oral melt tablet contained 0.5 mg of Compound I.

| | |
|---|---|
| Compound I | 0.5 g of $C_{28}H_{30}ClN_5O_2$ |
| Microcrystalline cellulose PH101 | 10 g |
| Mannitol | 80 g |
| Croscarmellose Sodium | 10 g |
| Water | q.s. |
| Magnesium stearate | 1.0 g |
| Silicon dioxide | 1.0 g |
| Formulated into | 1000 tablets |

Formulation 3. Each oral melt tablet contained 1.0 mg of Compound I.

| | |
|---|---|
| Compound I | 1.0 g of $C_{28}H_{30}ClN_5O_2$ |
| Microcrystalline cellulose PH101 | 10 g |
| Mannitol | 80 g |
| Croscarmellose Sodium | 10 g |
| Water | q.s. |
| Magnesium stearate | 1.0 g |
| Silicon dioxide | 1.0 g |
| Formulated into | 1000 tablets |

Exemplary sustained release tablet formulations are shown below.

Formulation 1. Each sustained release tablet contained 0.25 mg of Compound I.

| | |
|---|---|
| Compound I | 0.25 g of $C_{28}H_{30}ClN_5O_2$ |
| Microcrystalline cellulose PH101 | 20 g |
| Lactose | 70 g |
| Hydroxypropyl methylcellulose | 40 g |
| Polyvinylpyrrolidone K30 | 6 g |
| Magnesium stearate | 1.0 g |
| Silicon dioxide | 1.0 g |
| Formulated into | 1000 tablets |

Manufacturing Process:
(1) Compound I and the additives were weighed;
(2) They were sufficiently mixed for 15 minutes;
(3) Pelleting was done;
(4) The obtained tablets were coated and then packaged.

Formulation 2. Each sustained release tablet contained 0.5 mg of Compound I.

| | |
|---|---|
| Compound I | 0.5 g of $C_{28}H_{30}ClN_5O_2$ |
| Microcrystalline cellulose PH101 | 20 g |
| Lactose | 70 g |
| Hydroxypropyl methyl cellulose | 40 g |
| Polyvinylpyrrolidone K30 | 6 g |
| Magnesium stearate | 1.0 g |
| Silicon dioxide | 1.0 g |
| Formulated into | 1000 tablets |

Formulation 3. Each sustained release tablet contained 1.0 mg of Compound I.

| | |
|---|---|
| Compound I | 1.0 g of $C_{28}H_{30}ClN_5O_2$ |
| Microcrystalline cellulose PH101 | 20 g |
| Lactose | 70 g |
| Hydroxypropyl methyl cellulose | 40 g |
| Polyvinylpyrrolidone K30 | 6 g |
| Magnesium stearate | 1.0 g |
| Silicon dioxide | 1.0 g |
| Formulated into | 1000 tablets |

Exemplary micro-capsule formulations are shown below.

Formulation 1. Each gram of micro-capsules contained 0.25 mg of Compound I.

| | |
|---|---|
| Compound I | 0.25 g of $C_{28}H_{30}ClN_5O_2$ |
| Stearic acid | 900 g |
| 10% ethyl cellulose in ethanol | 1000 mL |
| 95% ethanol | q.s. |
| Formulated into | 1000 g |

Manufacturing Process:

(1) Stearic acid was weighed and melted in a water bath;

(2) Compound I was weighed and then stirred with and dissolved in 10% ethyl cellulose in ethanol;

(3) Ethanol (q.s.) was added to the mixture obtained in step (2), and the resultant mixture was added to the melt stearic acid; the mixture was kept heated in the water bath until uniform liquid was obtained;

(4) The liquid were sprayed and cooled, with micro-capsules settled out;

(5) The micro-capsules were collected.

Formulation 2. Each gram of micro-capsules contained 0.5 mg of Compound I.

| | |
|---|---|
| Compound I | 0.5 g of $C_{28}H_{30}ClN_5O_2$ |
| Stearic acid | 900 g |
| 10% ethyl cellulose in ethanol | 1000 mL |
| 95% ethanol | q.s. |
| Formulated into | 1000 g |

Formulation 3. Each gram of micro-capsules contained 1.0 mg of Compound I.

| | |
|---|---|
| Compound I | 1.0 g of $C_{28}H_{30}ClN_5O_2$ |
| Stearic acid | 900 g |
| 10% ethyl cellulose in ethanol | 1000 mL |
| 95% ethanol | q.s. |
| Formulated into | 1000 g |

Exemplary liposome formulation is shown below.

Formulation 1. Each milliliter of liposomes contained 0.25 mg of Compound I.

| | |
|---|---|
| Compound I | 0.25 g of $C_{28}H_{30}ClN_5O_2$ |
| Soybean lecithin | 20 g |
| Cholesterol | 5 g |
| Polyethylene glycol 4000 | 100 mL |
| Ethanol | q.s. |
| Formulated into | 1000 mL |

Manufacturing Process:

(1) Soybean lecithin and cholesterol were weighed and dissolved in ethanol (q.s.);

(2) Compound I was weighed and ultrasonically dissolved in polyethylene glycol 4000; water was added to the solution to a total volume of 800 mL;

(3) The solution obtained in step (1) was slowed introduced into the solution obtained in step (2), and the resultant mixture was stirred at 55° C.; ethanol was completely removed, and water was added to a total volume of 1000 mL.

Exemplary micelle formulation is shown below.

Formulation 1. Each milliliter of micelle contained 0.25 mg of Compound I.

| | |
|---|---|
| Compound I | 0.25 g of $C_{28}H_{30}ClN_5O_2$ |
| Soybean lecithin | 10 g |
| Ethanol | 100 g |
| Polyethylene glycol 4000 | 50 g |
| Water added to | 1000 mL |
| Formulated into | 1000 mL |

Manufacturing Process:

(1) Compound I, soybean lecithin and polyethylene glycol 4000 were weighed and dissolved in ethanol;

(2) Water was added to a total volume of 1000 mL to dilute the obtained mixture.

Exemplary solution formulations are shown below.

Formulation 1. Each 5 milliliter of the solution contained 0.1 mg of Compound I.

| | |
|---|---|
| Compound I having $D_{90}$ of 5 μm | 0.1 g of $C_{28}H_{30}ClN_5O_2$ |
| Sodium dodecyl sulfate | 1.0 g |
| Edetate disodium | 1.0 g |
| Citric acid | 2.0 g |
| Aspartame | 5.0 g |
| Aquae pro injectione | Added to 5000 mL |
| Formulated into | 1000 ampoules |

Formulation 2. Each 5 milliliter of the solution contained 0.25 mg of Compound I.

| | |
|---|---|
| Compound I having $D_{90}$ of 5 μm | 0.25 g of $C_{28}H_{30}ClN_5O_2$ |
| Sodium dodecyl sulfate | 2.5 g |
| Edetate disodium | 1.0 g |
| Citric acid | 2.0 g |
| Aspartame | 5.0 g |
| Aquae pro injectione | Added to 5000 mL |
| Formulated into | 1000 ampoules |

Formulation 3. Each 5 milliliter of the solution contained 0.5 mg of Compound I.

| | |
|---|---|
| Compound I having $D_{90}$ of 5 μm | 0.5 g of $C_{28}H_{30}ClN_5O_2$ |
| Sodium dodecyl sulfate | 5.0 g |
| Edetate disodium | 1.0 g |
| Citric acid | 2.0 g |
| Aspartame | 5.0 g |
| Aquae pro injectione | Added to 5000 mL |
| Formulated into | 1000 ampoules |

Formulation 4. Each 5 milliliter of the solution contained 1.0 mg of Compound I.

| | |
|---|---|
| Compound I having $D_{90}$ of 5 μm | 1.0 g of $C_{28}H_{30}ClN_5O_2$ |
| Sodium dodecyl sulfate | 10.0 g |
| Edetate disodium | 1.0 g |
| Citric acid | 2.0 g |
| Aspartame | 5.0 g |
| Aquae pro injectione | Added to 5000 mL |
| Formulated into | 1000 ampoules |

Manufacturing Process:

(1) Compound I and the additives were weighed;

(2) Sodium dodecyl sulfate was dissolved in the Aquae pro injection (q.s.) and then added with Compound I which was stirred to dissolve; then edetate disodium, citric acid and aspartame were added into and dissolved in the resultant solution;

(3) The obtained solution was subject to filtration and sterilization;

(4) The solution was filled in ampoules, 5 mL for each;

(5) The ampoules were packaged.

Example 3. Effect of Particle Size on Absorption

Example 3-1. Effect of Particle Size on Absorption

Compound I with different formulations and/or different $D_{90}$ values was compared for absorptions in male SD rats.

Samples to test: Compound I was prepared by the method as described in Example 1 of WO2014094664A1, and then pulverized to provide Compound I samples having $D_{90}$ of 538 nm, 3.8 μm, 21.7 μm, 41.5 μm and 71.6 μm, respectively; immediately before the tests, these samples were suspended in 0.5% MC to obtain 1 mg/mL suspensions.

Solutions: 5% DMSO+95% (solution containing 6% HP-β-CD)

Solid dispersions: Compound I: Polyvinylpyrrolidone K30=1:8 (w/w)

The SD rats were intragastrically given a single dose of the test samples at a dose of 1.0 mg/kg, and blood was collected prior to the administration and 30 min, 1 h, 2 h, 4 h, 6 h, 8 h, 10 h, and 24 h after the administration.

The formulation for intravenous injection was a solution where Compound I was dissolved in 5% DMSO+95% (6% HP-β-CD solution), and SD rats were administered at a dose of 2 mg/kg. The rats' blood samples were collected prior to the administration and 5 min, 15 min, 30 min, 1 h, 2 h, 4 h, 6 h, 8 h, and 24 h after the administration.

Blood collection: The animals were fixed and had their tails warmed in a water bath 10 min prior to blood collection; about 100 μL of blood was collected through the tail vein for each animal and put into an anticoagulation tube containing hepatin; the blood samples were subject to centrifugation at 8000 rpm for 6 min at 4° C. to obtain plasma samples, which had to be obtained within 30 minutes after blood was collected; the plasma samples were stored in a freezer at −80° C. for future tests.

Sample analysis: 50 μL of each plasma sample from the freezer was transferred to a centrifugal tube; 100 μL of water and 400 μL of MTBE standard solution (50 ng/mL) were added into the tube and well mixed with the plasma; the obtained mixture was mixed for 10 minutes using a vortex mixer and then subject to centrifugation for 10 minutes (4000 r/min); 300 μL of the supernatant was transferred to another centrifugal tube and blown dry with nitrogen gas; the resultant substance was dissolved in 200 μL of a solution consisting of methanol and water at a ratio of 1:1, of which 204 was used for the LC-MS/MS test.

Data processing: The compound concentration was output by Analyst 1.6.1 (AB Sciex); the means, standard deviations, and variation coefficients were calculated using Microsoft Excel (no calculation needed if these parameters were directly output by Analyst 1.6.1), and pharmacokinetic parameters were determined using the NCA analysis object in Pharsight Phoenix 6.3.

Results and Discussion

TABLE 1

Absorption of Compound I of different particle sizes in male SD rats

| Test sample | $AUC_{INF}$ (ng * h/mL) | BA % |
|---|---|---|
| Solution | 1276 | 81.6 |
| Solid dispersion | 1202 | 76.9 |
| Compound I with $D_{90}$ of 538 nm | 1287 | 82.3 |
| Compound I with $D_{90}$ of 3.8 μm | 1045 | 66.9 |
| Compound I with $D_{90}$ of 21.7 μm | 854 | 54.6 |
| Compound I with $D_{90}$ of 41.5 μm | 545 | 34.8 |
| Compound I with $D_{90}$ of 72.0 μm | 207 | 13.2 |

Note:
The solution, when administered by intravenous injection at a dose of 2.0 mg/kg, resulted in an $AUC_{INF}$ of 3126 ng * h/mL.

Conclusion

It can be seen from the Table above that, the lower the particle size of Compound I was, the higher bioavailability would be. When Compound I had a particle size of 21.7 µm, bioavailability reached 54.6%, meeting the clinic requirements.

Example 3-2. Effect of Particle Size on Absorption

Sample to test: Compound I having $D_{90}$ of 5 µm was suspended in 0.5% MC immediately before tests, to prepare 0.25 mg/mL suspension.
Animals: Three Beagle Dogs.
Method
Drug Administration and Blood Collection:
(1) All animals fasted for 12 h or longer before drug administration, and food was supplied 4 h after drug administration, with ad libitum access to water all the time. Animals were intragastrically given the test samples in a single dose at a dose of 0.5 mg/kg, and 200 µL of blood was collected for each animal, via the small saphenous vein, immediately prior to the administration (t=0) and 10 min, 30 min, 45 min, 1 h, 2 h, 4 h, 6 h, 8 h, 12 h, 24 h, 30 h, 48 h and 72 h after the administration. The collected blood was stored in a dry tube with heparin (normal saline containing 0.1% heparin sodium).
(2) Plasma preparation: The whole blood samples collected in step (1) were subject to centrifugation at a low speed (8000 r/min, 6 min, 4° C.) to separate the plasma (the whole blood was stored in a mobile freezer at about 0 to 4° C., and plasma had to be separated within 30 minutes after the blood collection), and the plasma was kept in dark in a freezer at −70° C. (or lower) for future analysis.
Sample analysis: 50 µL of each plasma sample from the freezer was transferred to a centrifugal tube; 100 µL of water and 400 µL of MTBE standard solution (50 ng/mL) were added into the tube and well mixed with the plasma; the obtained mixture was mixed for 10 minutes using a vortex mixer and then subject to centrifugation for 5 minutes (12000 r/min); 300 µL of the supernatant was transferred to another centrifugal tube and blown dry with nitrogen gas; the resultant substance was dissolved in 200 µL of a solution consisting of methanol and water at a ratio of 1:1, of which 20 µL was used for the LC-MS/MS measurement.
Data processing: The compound concentration was output by Analyst 1.6.1 (AB Sciex); the means, standard deviations, and variation coefficients were calculated using Microsoft Excel (no calculation needed if these parameters were directed output by Analyst 1.6.1), and pharmacokinetic parameters were determined using the NCA analysis object in Pharsight Phoenix 6.3.
Results:

TABLE 2

Absorption in Beagle dogs

| Test sample | Dose (mg/kg) | $AUC_{0-\infty}$ (ng * h/mL) | BA % |
|---|---|---|---|
| Compound I having $D_{90}$ of 5 µm | 0.5 | 506 | 57.4 |

Note:
The solution, when administered by intravenous injection at a dose of 1.0 mg/kg, resulted in an $AUC_{INF}$ of 1762 ng * h/mL.

Example 3-3. Additives had No Effect on Absorption

With the methods as described in Example 3-1, the capsule of Capsule formulation 6 as prepared in Example 2 was added in water to prepare a suspension with a concentration of 0.1 mg/ml, which was intragastrically given to SD rats in a single dose at a dose of 10 ml/kg (with an actual dose of 0.95 mg/kg).

The $AUC_{INF}$ was proved to be 821 ng*h/mL (the solution, when administered by intravenous injection at a dose of 2.0 mg/kg, resulted in an $AUC_{INF}$ of 3126 ng*h/mL), with bioavailability of 52.5%.

Example 3-4. Effect of Particle Size on Absorption

Samples to Test:
Capsule of Capsule formulation 5 as prepared in Example 2, 10 mg of Compound I per capsule.
Solutions: 5% DMSO+95% (6% HP-β-CD solution)
Animals: Four Beagle Dogs.
Method
Drug Administration and Blood Collection:
(1) Administration of capsules. All animals fasted for 12 h or longer before drug administration, and food was supplied 4 h after drug administration, with always ad libitum access to water. Beagle dogs were orally given the capsule of Capsule formulation 5 as prepared in Example 2 (two capsules for each Beagle, 10 mg of Compound I per capsule) in a single dose, and 200 µL of blood was collected for each animal, via the small saphenous vein, immediately prior to the administration (0 h) and 0.17 h, 0.50 h, 0.75 h, 1.0 h, 2.0 h, 4.0 h, 6.0 h, 8.0 h, 12 h and 24 h after the administration. The collected blood was stored in a dry tube with heparin (normal saline containing 0.1% heparin sodium).
(2) Plasma preparation. The whole blood samples collected in step (1) were subject to centrifugation at a low speed (8000 r/min, 6 min, 4° C.) to separate the plasma (the whole blood was stored in a mobile freezer at about 0 to 4° C., and plasma had to be separated within 30 minutes after the blood collection), and the plasma was kept in dark in a freezer at −70° C. (or lower) for future analysis.
Sample analysis: 50 µL of each plasma sample from the freezer was transferred to a centrifugal tube; 100 µL of water and 400 µL of MTBE standard solution (50 ng/mL) were added into the tube and well mixed with the plasma; the obtained mixture was mixed for 10 minutes using a vortex mixer and then subject to centrifugation for 5 minutes (12000 r/min); 300 µL of the supernatant was transferred to another centrifugal tube and blown dry with nitrogen gas; the resultant substance was dissolved in 200 µL of a solution consisting of methanol and water at a ratio of 1:1, of which 20 µL was used for the LC-MS/MS measurement.
Data processing: the compound concentration was output by Analyst 1.6.1 (AB Sciex); the means, standard deviations, and variation coefficients were calculated using Microsoft Excel (no calculation needed if these parameters were directed output by Analyst 1.6.1), and pharmacokinetic parameters were determined using the NCA analysis object in Pharsight Phoenix 6.3.
Results:

TABLE 3

Absorption of capsules in Beagle dogs

| Test sample | Dose (mg/kg) | $AUC_{0-\infty}$ (ng * h/mL) | BA % |
|---|---|---|---|
| Capsule of Capsule formulation 5 | 2.67 | 2361 | 50.2 |
| Capsule of Capsule formulation 5 | 2.63 | 2611 | 56.3 |
| Capsule of Capsule formulation 5 | 2.63 | 2314 | 49.9 |
| Capsule of Capsule formulation 5 | 2.78 | 3349 | 68.4 |
| Mean | 2.67 | 2659 | 56.5 |

Note:
The solutions, when administered by intravenous injection at a dose of 1.0 mg/kg, resulted in an $AUC_{INF}$ of 1762 ng * h/mL.

Example 3-5. Effect of Particle Size on Absorption

Sample to test: Capsule of Capsule formulation 6 as prepared in Example 2, 2.5 mg of Compound I per capsule.

Animals: Four Beagle Dogs.

The Beagle dog were orally administered with the capsule of Capsule formulation 6 as prepared in Example 2, one capsule for each Beagle dog, 2.5 mg of Compound I per capsule. Experiments were performed using the methods described in Example 3-3.

TABLE 4

Absorption of capsules in Beagle dogs

| Test sample | Dose (mg/kg) | $AUC_{0-\infty}$ (ng * h/mL) | BA % |
|---|---|---|---|
| Capsule of Capsule formulation 6 | 0.23 | 239 | 59.0 |

Note:
The solutions, when administered by intravenous injection at a dose of 1.0 mg/kg, resulted in an $AUC_{INF}$ of 1762 ng * h/mL.

Example 4. Effect of Surfactants on Absorption

Example 4-1. Effect of Surfactants on Absorption

Samples to test: 1 mg/mL suspensions were formulated by mixing Compound I and a surfactant at ratios of 1:5, 1:10 and 1:20, respectively.

SD rats were intragastrically given the test samples in a single dose at a dose of 1.0 mg/kg, and blood was collected prior to the administration and 30 min, 1 h, 2 h, 4 h, 6 h, 8 h, 10 h, and 24 h after the administration.

Blood collection: The animals were fixed and had their tails warmed in a water bath 10 min prior to blood collection; about 100 μL of blood was collected through the tail vein for each animal and put into an anticoagulation tube containing hepatin; the blood samples were subject to centrifugation at 8000 rpm for 6 min at 4° C. to obtain plasma samples, which had to be obtained within 30 minutes after blood was collected; the plasma samples were stored in a freezer at −80° C. for future tests.

Sample analysis: 50 μL of each plasma sample from the freezer was transferred to a centrifugal tube; 100 μL of water and 400 μL of MTBE standard solution (50 ng/mL) were added into the tube and well mixed with the plasma; the obtained mixture was mixed for 10 minutes using a vortex mixer and then subject to centrifugation for 5 minutes (12000 r/min); 300 μL of the supernatant was transferred to another centrifugal tube and blown dry with nitrogen gas; the resultant substance was dissolved in 200 μL of a solution consisting of methanol and water at a ratio of 1:1, of which 20 μL was used for the LC-MS/MS measurement.

Data processing: the compound concentration was output by Analyst 1.6.1 (AB Sciex); the means, standard deviations, and variation coefficients were calculated using Microsoft Excel (no calculation needed if these parameters were directed output by Analyst 1.6.1), and pharmacokinetic parameters were determined using the NCA analysis object in Pharsight Phoenix 6.3.

Results

TABLE 5

Effect of the surfactant on Absorption (Compound I:the surfactant = 1:10)

| Surfactant | Dose (mg/kg) | $AUC_{INF}$ (ng * h/mL) | BA % |
|---|---|---|---|
| Glycerol | 0.87 | 657 | 48.3 |
| Propylene glycol | 0.89 | 457 | 32.9 |
| Polyvinyl alcohol | 0.87 | 603 | 44.3 |
| Polyethylene glycol 400 | 0.97 | 613 | 40.0 |
| Sodium dodecyl sulfonate | 0.99 | 831 | 53.7 |
| Sodium dodecyl sulfate | 1.01 | 964 | 61.1 |
| Polyoxyl(40) stearate | 0.88 | 427 | 31.0 |
| PVP $K_{30}$ | 0.94 | 608 | 41.4 |
| Carbomer | 0.91 | 289 | 20.1 |
| Polysorbate 80 | 0.9 | 654 | 46.5 |
| Poloxamer 188 | 0.97 | 712 | 47.0 |
| Hydroxypropyl cellulose | 0.92 | 535 | 37.2 |
| Hydroxypropyl methyl cellulose | 0.91 | 483 | 33.6 |
| Kolliphor HS15 | 0.99 | 536 | 34.6 |
| Cholic acid | 0.96 | 701 | 46.7 |
| Benzalkonium chloride | 0.83 | 768 | 59.2 |
| hydroxypropyl-β-cyclodextrin | 0.91 | 350 | 24.6 |

Note:
The solution, when administered by intravenous injection at a dose of 2.0 mg/kg, resulted in an $AUC_{INF}$ of 3126 ng * h/mL.

TABLE 6

Effect of the surfactant on Absorption (Compound I:the surfactant = 1:20)

| Surfactant | Dose (mg/kg) | $AUC_{INF}$ (ng * h/mL) | BA % |
|---|---|---|---|
| Benzalkonium chloride | 0.93 | 1402 | 96.5 |
| Sodium dodecyl sulfonate | 0.98 | 953 | 62.2 |
| Sodium dodecyl sulfate | 0.93 | 1297 | 89.2 |

Note:
The solution, when administered by intravenous injection at a dose of 2.0 mg/kg, resulted in an $AUC_{INF}$ of 3126 ng * h/mL.

TABLE 7

Effect of the surfactant on Absorption (Compound I:the surfactant = 1:5)

| Ratio | Surfactant | Dose (mg/kg) | $AUC_{INF}$ (ng * h/mL) | BA % |
|---|---|---|---|---|
| 1:5 | Benzalkonium chloride | 0.80 | 855 | 68.4 |
| 1:5 | Sodium dodecyl sulfonate | 0.96 | 968 | 64.5 |

Note:
The solution, when administered by intravenous injection at a dose of 2.0 mg/kg, resulted in an $AUC_{INF}$ of 3126 ng * h/mL.

Example 4-2. Effect of Surfactants on Absorption

Samples to test: Tablet of Tablet formulation 3 prepared in Example 2, 2.5 mg of Compound I per tablet.

Solutions: 5% DMSO+95% (6% HP-β-CD solution), intravenous (IV) administration.

Animals: Eight Beagle Dogs, Four for Each Group.

Method

Drug Administration and Blood Collection:

(1) All animals fasted for 12 h or longer before drug administration, and food was supplied 4 h after drug administration, with always ad libitum access to water. Beagle dogs were orally given the tablets prepared in Example 2, two tablets for each Beagle dog, 2.5 mg of Compound I per tablet, and 200 μL of blood was collected for each animal, via the small saphenous vein, 30 min, 45 min, 1 h, 2 h, 4 h, 6 h, 8 h, 12 h, and 24 h after the administration. The collected blood samples were stored in a dry tube with K2EDTA.

For the group with intravenous (IV) administration, blood was collected 5 min, 15 min, 30 min, 1 h, 2 h, 4 h, 6 h, 8 h, 12 h, and 24 h after the administration.

(2) Plasma preparation: The whole blood samples collected in step (1) were subject to centrifugation at a low speed (8000 r/min, 6 min, 4° C.) to separate the plasma (the whole blood was stored in a mobile freezer at about 0 to 4° C., and plasma had to be separated within 30 minutes after the blood collection), and the plasma was kept in dark in a freezer at −70° C. (or lower) for future analysis.

Sample analysis: 50 μL of each plasma sample from the freezer was transferred to a centrifugal tube; 100 μL of water and 400 μL of MTBE standard solution (50 ng/mL) were added into the tube and well mixed with the plasma; the obtained mixture was mixed for 10 minutes using a vortex mixer and then subject to centrifugation for 5 minutes (12000 r/min); 300 μL of the supernatant was transferred to another centrifugal tube and blown dry with nitrogen gas; the resultant substance was dissolved in 200 μL of a solution consisting of methanol and water at a ratio of 1:1, of which 20 μL was used for the LC-MS/MS measurement.

Data processing: the compound concentration was output by Analyst 1.6.1 (AB Sciex); the means, standard deviations, and variation coefficients were calculated using Microsoft Excel (no calculation needed if these parameters were directed output by Analyst 1.6.1), and pharmacokinetic parameters were determined using the NCA analysis object in Pharsight Phoenix 6.3.

Results

TABLE 8

Absorption in Beagle dogs

| Formulation | Dose (mg/kg) | $AUC_{INF}$ (ng * h/mL) | F % |
|---|---|---|---|
| Tablet formulation 3 | 0.59 | 1100 | 77.4 |
| IV group | 0.6 | 1445 | NA |

Example 4-3. Effect of Surfactants on Absorption

Sample to Test:

Self-emulsifying drug delivery system (SEDDS): CompoundI:ethanol:Kolliphor EL:Miglyol 812N=10 mg: 1 g: 5 g: 4 g.

Solutions: 5% DMSO+95% (6% HP-β-CD solution)

SD rats were intragastrically given the test samples in a single dose at a dose of 1.0 mg/kg, and blood was collected prior to the administration and 30 min, 1 h, 2 h, 4 h, 6 h, 8 h, 10 h, and 24 h after the administration.

The formulation for intravenous injection was a solution where Compound I was dissolved in 5% DMSO+95% (6% HP-β-CD solution), and SD rats were administered at a dose of 2 mg/kg. The rats' blood samples were collected prior to the administration and 5 min, 15 min, 30 min, 1 h, 2 h, 4 h, 6 h, 8 h, and 24 h after the administration.

Blood collection: The animals were fixed and had their tails warmed in a water bath 10 min prior to blood collection; about 100 μL of blood was collected through the tail vein for each animal and put into an anticoagulation tube containing hepatin; the blood samples were subject to centrifugation at 8000 rpm for 6 min at 4° C. to obtain plasma samples, which had to be obtained within 30 minutes after blood was collected; the plasma samples were stored in a freezer at −80° C. for future tests.

Sample analysis: 50 μL of each plasma sample from the freezer was transferred to a centrifugal tube; 100 μL of water and 400 μL of MTBE standard solution (50 ng/mL) were added into the tube and well mixed with the plasma; the obtained mixture was mixed for 10 minutes using a vortex mixer and then subject to centrifugation for 5 minutes (12000 r/min); 300 μL of the supernatant was transferred to another centrifugal tube and blown dry with nitrogen gas; the resultant substance was dissolved in 200 μL of a solution consisting of methanol and water at a ratio of 1:1, of which 20 μL was used for the LC-MS/MS measurement.

Data processing: the compound concentration was output by Analyst 1.6.1 (AB Sciex); the means, standard deviations, and variation coefficients were calculated using Microsoft Excel (no calculation needed if these parameters were directed output by Analyst 1.6.1), and pharmacokinetic parameters were determined using the NCA analysis object in Pharsight Phoenix 6.3.

Results and Conclusions

The rats orally administered with the SEDDS drug had $AUC_{INF}$ of 1297 ng*h/mL (for the solution intravenously given at a dose of 2.0 mg/kg, $AUC_{INF}$ of 3126 ng*h/mL was generated), with bioavailability being 83.0%.

Example 5. Toxicity and Pharmacokinetic Studies in SD Rats Intragastrically Administered with Compound I for 13 Weeks and Recovered for 4 Weeks Sample to test: Solid dispersion of Compound I (Compound I:PVPK30=1:8 (w/w))

Animals: SD Rats, SPF Level.

Method:

Two hundred and twenty SD rats were used in the studies. Three groups, i.e., high dose group, intermediate dose group and low dose group, were administered with Compound I with following doses, 20 males and 20 females for each group. In specific, male animals were given the suspension at the doses of 3, 9 and 30 mg/kg/day, respectively, while the females were administered at the doses of 1, 3, and 10 mg/kg/day, respectively. The animals in the control group, 20 males and 20 females, were given purified water. All animals fasted overnight before blood collections and anatomical examinations.

In addition, for the pharmacokinetic study, 9 males and 9 females were assigned into the administration group, while 3 males and 3 females were for the control group.

Results and Conclusions

TABLE 9

Serum potassium (K$^+$) and $AUC_{0-24\,h}$ levels in SD rats intragastrically administered with Compound I for 13 weeks

| Gender | Dose (mg/kg) | K$^+$(mmol/L) (Mean ± SD) | $AUC_{0-24\,h}$ (ng * h/mL) |
|---|---|---|---|
| Male | 0 | 5.1 ± 0.3 | / |
|  | 3 | 5.0 ± 0.3 | 5430 |
|  | 9 | 5.0 ± 0.3 | 16500 |
|  | 30 | 5.1 ± 0.2 | 49900 |
| Female | 0 | 4.2 ± 0.3 | / |
|  | 1 | 4.4 ± 0.4 | 4080 |
|  | 3 | 4.4 ± 0.3 | 15500 |
|  | 10 | 4.5 ± 0.2 | 43600 |

Note:
"/" means n.a. (not applicable).

Based on results above, the NOAEL (no observed adverse effect level) was 30 mg/kg/day in male animals and 10 mg/kg/day in females, with the corresponding $AUC_{0-24h}$ being 49900 ng*h/mL and 43600 ng*h/mL, respectively, under which AUC level no obvious abnormal serum potassium level was observed.

Example 6. Efficacy Test in Salt-Sensitive Rats with Salt Induced Renal Injury Animals: Male Dahl/Ss Rats
Test Article and Formulation:
Solid dispersions of Compound I (Compound I:PVPK30=1:8 (w/w)): Solid dispersions of Compound I was formulated with suitable amount of sterile water for injection into suspensions having concentrations of 0.03, 0.10, 0.30 and 1.00 mg/mL, respectively. The suspensions were prepared immediately before use.

The Dahl/ss rats were randomly divided into 6 groups based on the blood pressures tested before drug administration, i.e., Control group 1 with normal animals (n=10), Control group 2 with animals having induced renal injury (4% NaCl, n=12), Treatment groups with doses at 0.3 mg/kg/day (n=11), 1 mg/kg/day (n=11), 3 mg/kg/day (n=11) and 10 mg/kg/day (n=11), respectively, wherein n represents number of animals.

Method
The Dahl/ss rats were fed Research diet AIN-93G containing 4% NaCl to induce hypertensive nephropathy, so as to test the in vivo pharmacodynamics activity of Compound I.

One week before the experiment, the blood pressures were measured twice in rats by the tail-cuff blood pressure measurement so that rats could accommodate to the blood pressure monitoring operation. Then, immediately before the test, the blood pressure was determined and used as the baseline value. According to the baseline blood pressures, the rats were randomly divided into groups. On the next day, the animals in Control group 2 and the treatment groups were fed Research diet AIN-93G containing 4% NaCl and water, ad libitum, to induce the renal injury model. The model build took 42 days. The animals in Control group 1 was given the normal AIN-93G diet.

The animals in the treatment groups were intragastrically given Compound I twice a day at doses of 0.3, 1, 3 and 10 mg/kg/day, respectively, with the suspensions of Compound I being administered in a volume of 5 mL/kg per dose. The two control groups were given an equal amount of sterile water for injection.

Blood pressure (systolic blood pressure, SBP) measurement: Blood pressure was measured for 6 weeks, once a week, and the blood pressure changes in these groups were analyzed.

Pathological examination for the kidney and heart: At the end of the study, rats were sacrificed painlessly, from which bilateral kidneys and the heart were collected for histopathological analysis. The kidneys were stained using Hematoxylin-Eosin (HE) to semi-quantitatively evaluate renal injuries. The thickness of the left ventricular wall was measured for each heart to analyze the heart injury.

Further, blood samples at 0 h, 1 h, 2 h, 4 h, 6 h, 8 h, 10 h, and 24 h post the last administration were collected from the tail vein of rats before the end of the study. Blood samples were put into a low-temperature high-speed centrifuge and centrifuged for 6 min at 4° C., 8000 rpm. Plasma samples were collected and stored in a freezer at −80° C. until plasma drug concentration were measured.

Results and Conclusions

Figure 2:
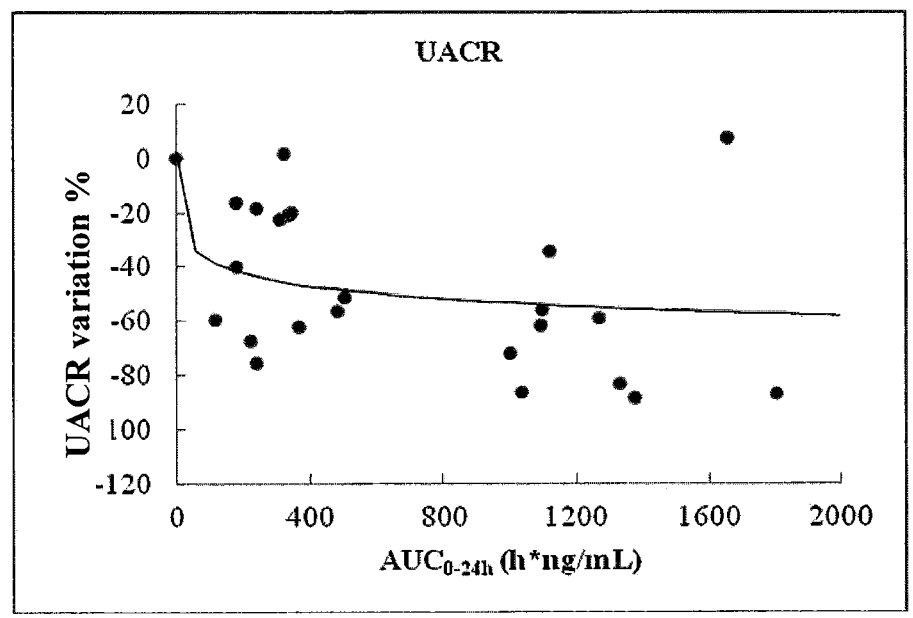
FIG. 2 is a curve showing the correlation between UACR variation based on baselines and $AUC_{0-24}$ in a DSS rat model with hypertension and renal injury induced by a high content of salts.

According to the test results, Blood pressure (SBP) or Urine albumin-to-creatinine ratio (UACR) vs. $AUC_{0-24}$ curve was plotted (see FIG. 1 and FIG. 2).

The SBP or UACR vs. $AUC_{0-24}$ curve showed an undulation point at 100 h*ng/mL of AUC after which the curve tended to be flat and SBP and UACR were significantly decreased. It was indicated that Compound I had good efficacy and took effect when AUC reached 100 h*ng/mL.

Example 7. Safety, Tolerability, and Pharmacokinetics Studies in Healthy Subjects with a Single Dose Five groups of healthy subjects were given capsules at doses of 0.5 mg (1 capsule, 0.5 mg of Compound I per capsule), 1.0 mg (2 capsules, 0.5 mg of Compound I per capsule), 2.5 mg (1 capsule, 2.5 mg of Compound I per capsule), 10 mg (1 capsule, 10 mg of Compound I per capsule), and 30 mg (3 capsules, 10 mg of Compound I per capsule), each group containing 8 subjects. The drug administration was done only once.

The capsules mentioned above were the ones prepared in Example 2, i.e., the capsules of Capsule formulation 3 (0.5 mg of Compound I per capsule), Capsule formulation 4 (2.5 mg of Compound I per capsule), and Capsule formulation 5 (10 mg of Compound I per capsule).

Plasma samples were collected to measure plasma drug concentration, and the pharmacokinetic parameters were analyzed using the non-compartment model. Serum samples were collected to measure serum potassium levels.

Results
In the healthy subjects administered at the dose of 0.5 to 30 mg/day, $AUC_{0-24}$ of Compound I was 162.5 to 5016 ng*h/mL, and $T_{1/2}$ was about 60 hours, with no elevated serum potassium level observed.

TABLE 10

Pharmacodynamics results

| Pharmacodynamics parameters | Dose | | | | |
|---|---|---|---|---|---|
| | 0.5 mg | 1.0 mg | 2.5 mg | 10 mg | 30 mg |
| $AUC_{0-24}$ (h * ng/mL) | 162.5 | 396.7 | 639.8 | 3077 | 5016 |
| $T_{1/2}$ (h) | 61.5 | 60.9 | 53.3 | 52.8 | 73.9 |

Example 8. Safety, Tolerability, and Pharmacokinetics Studies in Healthy Subjects with Multiple Doses Two groups of healthy subjects were given capsules once a day at daily doses of 2.5 mg (1 capsule for each administration, 2.5 mg of Compound I per capsule), and 5.0 mg (2 capsules for each administration, 2.5 mg of Compound I per capsule), respectively, each group containing 6 subjects. The administration continued for 14 consecutive days. The capsules used in this study were of Capsule formulation 4 prepared in Example 2.

Plasma samples were collected to measure plasma drug concentration, and the pharmacokinetic parameters were analyzed using the non-compartment model. Serum samples were collected to measure serum potassium levels.

Results

In the healthy subjects administered in multiple doses at the daily dose of 2.5 mg/day, the average steady-state $AUC_{0-24}$ was 2865±821 ng*h/mL, with no elevated serum potassium level observed.

In the healthy subjects administered in multiple doses at the daily dose of 5.0 mg/day, the average steady-state $AUC_{0-24}$ was 6376±1028 ng*h/mL, with transient elevated serum potassium level observed in three subjects.

Example 9. Safety, Tolerability, and Pharmacokinetics Studies in Patients Having Chronic Kidney Disease The patients in this example were those having chronic kidney disease with symptoms of renal failure, proteinuria, acute kidney injury, glomerular nephritis, renal cyst, urinary frequency, renal calculus, obstructive uropathy, and etc. These patients also had other diseases or implications such as diabetes mellitus, hyperlipidemia, hypercholesterolemia, hypertension, peripheral vascular diseases, coronary artery disease, and etc.

These patients continued to take the medications that they had prior to the present clinical trial, the medications being, for example, angiotensin converting enzyme inhibitors, such as Lisinopril, Benazepril, Enalapril, and Enalapril Maleate; angiotensin II receptor blockers, such as Valsartan and Losartan; calcium channel blockers, such as Amlodipine, and Nifedipine; diuretics, such as Furosemide; beta-receptor blockers, such as Metoprolol succinate, Metoprolol tartrate, Carvedilol, and Atenolol; and antilipemic drugs, such as Simvastatin, Atorvastatin, Fenofibrate, Pravastatin, and Rosuvastatin.

In this example, the administration dose referred to the amount of Compound I, although the pharmaceutical composition was administered. Two groups of subjects were administered once a day for 56 consecutive days at the daily doses of 0.5 mg (1 capsule for each administration, 0.5 mg of Compound I per capsule) and 2.5 mg (1 capsule for each administration, 2.5 mg of Compound I per capsule), respectively, with 6 subjects for the 0.5 mg/day dose group and also 6 for the 2.5 mg/day dose group. The capsules used here were the capsules prepared in Example 2, i.e., the capsules of Capsule formulation 3 (the capsule with 0.5 mg of Compound I), and Capsule formulation 4 (the capsule containing 2.5 mg of Compound I).

Plasma samples were collected to measure plasma drug concentration, and the pharmacokinetic parameters were analyzed using the non-compartment model. Serum samples were collected to measure serum potassium levels.

Results

In the CKD patients administered in multiple doses at the daily dose of 0.5 mg, the average steady-state $AUC_{tau}$ was 652.5±232.2 ng*h/mL, with no elevated serum potassium level observed.

In the CKD patients administered in multiple doses at the daily dose of 2.5 mg, mild increase of the serum potassium level was observed in one subject. The average safe steady-state $AUC_{tau}$ was 2613±280 ng*h/mL in the patients.

Those CKD patients following multiple-dosing administrations at the dose of 0.5 mg/day or 2.5 mg/day showed significantly decrease in blood pressures and urine albumin-to-creatinine ratio (UACR). At the 8th week, the UACR was decreased by 58.9% and 50.7% in the two groups, respectively. The pharmaceutical composition of the present invention showed evident effect on kidney protection.

The CKD patients had the steady-state $AUC_{tau}$ of 105.6 ng*h/mL or more when administered for one day at the daily dose of 0.5 mg, and UACR was decreased by 30.5% or more compared to the baseline, indicating the efficacy of the pharmaceutical composition of the present invention.

TABLE 11

Pharmacodynamics results

| Pharmacodynamics parameter | Dose (mg) | | | | | | | | |
| --- | --- | --- | --- | --- | --- | --- | --- | --- | --- |
| | 0.1 | 0.15 | 0.2 | 0.25 | 0.3 | 0.5 | 1.0 | 2.0 | 2.5 |
| $AUC_{tau}$ (ng*h/mL) | | | | | | | | | |
| Actual $AUC_{tau}$ | / | / | / | / | / | 652.5 | / | / | 2613 |
| Predicated $AUC_{tau}$ | 130.5 | 195.8 | 261 | 326.3 | 391.5 | / | 1305 | 2610 | 3262.5 |

In the CKD patients taking the pharmaceutical composition of the present invention, $AUC_{tau}$ of Compound I was in the range of 188 ng*h/mL to 3173 ng*h/mL, suggesting excellent efficacy. Further, no elevated serum potassium level was observed. Thus, the pharmaceutical composition of the present invention met the clinical safety and efficacy requirements.

We claim:

1. A pharmaceutical composition, comprising: Compound I, 2-chloro-4-[(3S,3aR)-3-cyclopentyl-7-(4-hydroxylpiperidine-1-carbonyl)-3,3a,4,5-tetrahydro-2H-pyrazolo[3,4-f]quinolin-2-yl]benzonitrile:

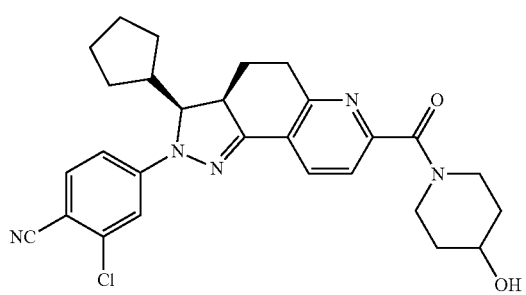 [SMILES: N#Cc1ccc(N2N=C3c4ccc(C(=O)N5CCC(O)CC5)nc4CC[C@@H]3[C@@H]2C2CCCC2)cc1Cl]

one or more surfactants selected from the group consisting of benzalkonium chloride, sodium lauryl sulfonate, sodium dodecyl sulfate, glycerol, cholic acid, poloxamer, polyvinyl alcohol, Polysorbate 80, PVP $K_{30}$ and polyethylene glycol, and one or more additional pharmaceutically acceptable carriers;
wherein the pharmaceutical composition is a unit dose formulation comprising 0.1 to 1.0 mg of Compound I;
the weight ratio of Compound I to the surfactant is between 1:0.1 to 1:20; and
the pharmaceutical composition is a tablet or a capsule.

2. The pharmaceutical composition according to claim 1, wherein the unit dose formulation comprises 0.1 to 0.5 mg of Compound I.

3. The pharmaceutical composition according to claim 2, wherein the daily dose is from unit dose formulation comprises 0.2 to 0.5 mg of Compound I.

4. The pharmaceutical composition according to claim 1, wherein the $D_{90}$ of Compound I is 25 μm or less.

5. The pharmaceutical composition according to claim 4, wherein the $D_{90}$ of Compound I is 10 μm or less.

6. The pharmaceutical composition according to claim 1, wherein the pharmaceutical composition comprises one or more surfactants selected from the group consisting of benzalkonium chloride, sodium lauryl sulfonate, and sodium dodecyl sulfate.

7. The pharmaceutical composition according to claim 6, wherein the pharmaceutical composition comprises one surfactant selected from the group consisting of benzalkonium chloride, sodium lauryl sulfonate, and sodium dodecyl sulfate.

8. The pharmaceutical composition according to claim 1, wherein the weight ratio is between 1:1 to 1:20.

9. The pharmaceutical composition according to claim 1, wherein the unit dose formulation comprises 0.1 mg of Compound I.

10. The pharmaceutical composition according to claim 1, wherein the unit dose formulation comprises 0.15 mg of Compound I.

11. The pharmaceutical composition according to claim 1, wherein the unit dose formulation comprises 0.2 mg of Compound I.

12. The pharmaceutical composition according to claim 1, wherein the unit dose formulation comprises 0.25 mg of Compound I.

13. The pharmaceutical composition according to claim 1, wherein the unit dose formulation comprises 0.3 mg of Compound I.

14. The pharmaceutical composition according to claim 1, wherein the unit dose formulation comprises 0.35 mg of Compound I.

15. The pharmaceutical composition according to claim 1, wherein the unit dose formulation comprises 0.4 mg of Compound I.

16. The pharmaceutical composition according to claim 1, wherein the unit dose formulation comprises 0.45 mg of Compound I.

17. The pharmaceutical composition according to claim 1, wherein the unit dose formulation comprises 0.5 mg of Compound I.

18. The pharmaceutical composition according to claim 1, wherein the unit dose formulation comprises 0.6 mg of Compound I.

19. The pharmaceutical composition according to claim 1, wherein the unit dose formulation comprises 0.7 mg of Compound I.

20. The pharmaceutical composition according to claim 1, wherein the unit dose formulation comprises 0.8 mg of Compound I.

21. The pharmaceutical composition according to claim 1, wherein the unit dose formulation comprises 0.9 mg of Compound I.

22. The pharmaceutical composition according to claim 1, wherein the unit dose formulation comprises 1.0 mg of Compound I.

* * * * *